(12) United States Patent
Opdyke et al.

(10) Patent No.: US 8,524,451 B2
(45) Date of Patent: Sep. 3, 2013

(54) **METHOD FOR REAL-TIME DETECTION OF *SALMONELLA* IN FOOD USING A CLEAVABLE CHIMERIC PROBE**

(75) Inventors: Jason Opdyke, Silver Spring, MD (US); Win Den Cheung, Olney, MD (US); Jun Li, Baltimore, MD (US)

(73) Assignee: Samsung Techwin Co., Ltd., Changwon (KR)

( * ) Notice: Subject to any disclaimer, the term of this patent is extended or adjusted under 35 U.S.C. 154(b) by 0 days.

(21) Appl. No.: 13/046,055

(22) Filed: Mar. 11, 2011

(65) Prior Publication Data

US 2011/0223598 A1    Sep. 15, 2011

Related U.S. Application Data

(60) Provisional application No. 61/312,873, filed on Mar. 11, 2010.

(51) Int. Cl.
*C12Q 1/68* (2006.01)
*C12P 19/34* (2006.01)
*C07H 21/04* (2006.01)

(52) U.S. Cl.
USPC ...... 435/6.12; 435/91.1; 435/91.2; 536/24.33

(58) Field of Classification Search
USPC .............................. 435/6.12, 91.1; 536/24.33
See application file for complete search history.

(56) References Cited

U.S. PATENT DOCUMENTS

| 4,965,188 A | * | 10/1990 | Mullis et al. | 435/6.12 |
| 2009/0325169 A1 | * | 12/2009 | Walder et al. | 435/6 |
| 2011/0117564 A1 | * | 5/2011 | Reshatoff et al. | 435/6 |

FOREIGN PATENT DOCUMENTS

WO    9304201    *    3/1993

OTHER PUBLICATIONS

Boyd et al. Journal of Bacteriology, 1997, vol. 179(6), p. 1985-1991.*
Harvey et al. Analytical Biochemistry, 2004, vol. 333(2), p. 246-255.*
Lowe et al. Nucleic Acid Research, 1990, vol. 18(7), p. 1757-1761.*
Nucleic acid sequence search reports (AC: AAQ34562 and U43273.*
Hoorfar et al. Journal of Clinical Microbiology, 2000, vol. 38(9), p. 3429-3435.*

* cited by examiner

*Primary Examiner* — Kenneth R. Horlick
*Assistant Examiner* — Joyce Tung
(74) *Attorney, Agent, or Firm* — Sughrue Mion, PLLC

(57) ABSTRACT

A method is described for the real-time detection of *Salmonella* species in foods and on surfaces. *Salmonella* are enriched in media to increase their cell density prior to analysis. DNA is recovered by lysis in the presence of azide, proteinase K, and detergent. Real-time detection of *Salmonella* species is performed in a PCR reaction using gene specific primers and a cleavable chimeric fluorescent probe. The method also describes an internal control to confirm the efficiency of nucleic acid amplification and detection. The method is amenable to medium and high throughput analysis.

54 Claims, 13 Drawing Sheets

SEQUENCE LISTING

<160> NUMBER OF SEQ ID NOS: 30

<210> SEQ ID NO 1
<211> LENGTH: 20
<212> TYPE: DNA
<213> ORGANISM: Artificial Sequence
<220> FEATURE:
<223> OTHER INFORMATION: primer that anneals to Salmonella invA gene

<400> SEQUENCE: 1
tcgtcattcc attacctacc                                               20

<210> SEQ ID NO 2
<211> LENGTH: 24
<212> TYPE: DNA
<213> ORGANISM: Artificial Sequence
<220> FEATURE:
<223> OTHER INFORMATION: primer that anneals to Salmonella invA gene

<400> SEQUENCE: 2
tactgatcga taatgccaga cgaa                                          24

<210> SEQ ID NO 3
<211> LENGTH: 20
<212> TYPE: DNA
<213> ORGANISM: Artificial Sequence
<220> FEATURE:
<223> OTHER INFORMATION: primer that anneals to Salmonella invA gene

<400> SEQUENCE: 3
acgcgcttga tgagctttac                                               20

<210> SEQ ID NO 4
<211> LENGTH: 20
<212> TYPE: DNA
<213> ORGANISM: Artificial Sequence
<220> FEATURE:
<223> OTHER INFORMATION: primer that anneals to Salmonella invA gene

<400> SEQUENCE: 4
gttgtaccgt ggcatgtctg                                               20

<210> SEQ ID NO 5
<211> LENGTH: 20
<212> TYPE: DNA
<213> ORGANISM: Artificial Sequence
<220> FEATURE:
<223> OTHER INFORMATION: primer that anneals to Salmonella invA gene

<400> SEQUENCE: 5
catatgctgg accaactgga                                               20

<210> SEQ ID NO 6
<211> LENGTH: 20
<212> TYPE: DNA
<213> ORGANISM: Artificial Sequence
<220> FEATURE:
<223> OTHER INFORMATION: primer that anneals to Salmonella invA gene

<400> SEQUENCE: 6
cggaaacacg ttcgcttaat                                               20

<210> SEQ ID NO 7
<211> LENGTH: 19
<212> TYPE: DNA

```
<213> ORGANISM: Artificial Sequence
<220> FEATURE:
<223> OTHER INFORMATION: FRET probe that anneals to Salmonella invA gene
<220> FEATURE:
<221> NAME/KEY: misc_feature
<222> LOCATION: (1)..(1)
<223> OTHER INFORMATION: 6-carboxyfluorescein donor chromophore
<220> FEATURE:
<221> NAME/KEY: misc_feature
<222> LOCATION: (1)..(6)
<223> OTHER INFORMATION: DNA sequence
<220> FEATURE:
<221> NAME/KEY: misc_feature
<222> LOCATION: (7)..(11)
<223> OTHER INFORMATION: RNA sequence
<220> FEATURE:
<221> NAME/KEY: misc_feature
<222> LOCATION: (12)..(19)
<223> OTHER INFORMATION: DNA sequence
<220> FEATURE:
<221> NAME/KEY: misc_feature
<222> LOCATION: (19)..(19)
<223> OTHER INFORMATION: Black Hole Quencher  for short wavelength
      emission from Integrated DNA Technologies (Coralvile, IA)

<400> SEQUENCE: 7
cgatcaggaa atcaaccag                                              19

<210> SEQ ID NO 8
<211> LENGTH: 19
<212> TYPE: DNA
<213> ORGANISM: Artificial Sequence
<220> FEATURE:
<223> OTHER INFORMATION: FRET probe that anneals to Salmonella invA gene
<220> FEATURE:
<221> NAME/KEY: misc_feature
<222> LOCATION: (1)..(1)
<223> OTHER INFORMATION: FAM: 6-Carboxyfluorescein donor chromophore
<220> FEATURE:
<221> NAME/KEY: misc_feature
<222> LOCATION: (1)..(8)
<223> OTHER INFORMATION: DNA sequence
<220> FEATURE:
<221> NAME/KEY: misc_feature
<222> LOCATION: (9)..(12)
<223> OTHER INFORMATION: RNA sequence
<220> FEATURE:
<221> NAME/KEY: misc_feature
<222> LOCATION: (13)..(19)
<223> OTHER INFORMATION: DNA sequence
<220> FEATURE:
<221> NAME/KEY: misc_feature
<222> LOCATION: (13)..(13)
<223> OTHER INFORMATION: Iowa Black FQ quencher

<400> SEQUENCE: 8
aggtaaccga aaacaagcc                                              19

<210> SEQ ID NO 9
<211> LENGTH: 28
<212> TYPE: DNA
<213> ORGANISM: Artificial Sequence
<220> FEATURE:
<223> OTHER INFORMATION: primer that anneals to Salmonella invA gene

<400> SEQUENCE: 9
ctcgcgcgta gattgccatg cgtagagc                                    28

<210> SEQ ID NO 10
<211> LENGTH: 28
<212> TYPE: DNA
<213> ORGANISM: Artificial Sequence
<220> FEATURE:
<223> OTHER INFORMATION: primer that anneals to Salmonella invA gene
```

<400> SEQUENCE: 10
gtgaacccac ttgcctttgc gtcttaat                                                28

<210> SEQ ID NO 11
<211> LENGTH: 19
<212> TYPE: DNA
<213> ORGANISM: Artificial Sequence
<220> FEATURE:
<223> OTHER INFORMATION: FRET prober that anneals to Salmonella invA
      gene
<220> FEATURE:
<221> NAME/KEY: misc_feature
<222> LOCATION: (1)..(8)
<223> OTHER INFORMATION: DNA sequence
<220> FEATURE:
<221> NAME/KEY: misc_feature
<222> LOCATION: (1)..(1)
<223> OTHER INFORMATION: TYE 665: variant of Cy5 from Integrated DNA
      Technologies (Coralvile, IA) chromophore donor
<220> FEATURE:
<221> NAME/KEY: misc_feature
<222> LOCATION: (9)..(12)
<223> OTHER INFORMATION: RNA sequence
<220> FEATURE:
<221> NAME/KEY: misc_feature
<222> LOCATION: (13)..(19)
<223> OTHER INFORMATION: DNA sequence
<220> FEATURE:
<221> NAME/KEY: misc_feature
<222> LOCATION: (19)..(19)
<223> OTHER INFORMATION: IABFQ: Black Hole Quencher for short wavelength
      emission from Integrated DNA Technologies (Coralvile, IA)

<400> SEQUENCE: 11
aggtaaccga aaacaagcc                                                          19

<210> SEQ ID NO 12
<211> LENGTH: 1950
<212> TYPE: DNA
<213> ORGANISM: Salmonella enterica

<400> SEQUENCE: 12
aacagtgctc gtttacgacc tgaattactg attctggtac taatggtgat gatcatttct            60
atgttcgtca ttccattacc tacctatctg gttgatttcc tgatcgcact gaatatcgta           120
ctggcgatat tggtgtttat ggggtcgttc tacattgaca gaatcctcag ttttcaacg            180 tttcctgcgg tactgttaat taccacgctc tttcgtctgg cattatcgat cagtaccagc           240
cgtcttatct tgattgaagc cgatgccggt gaaattatcg ccacgttcgg gcaattcgtt           300
attggcgata gcctggcggt gggttttgtt gtcttctcta ttgtcaccgt ggtccagttt           360
atcgttatta ccaaaggttc agaacgcgtc gcggaagtcg cggcccgatt ttctctggat           420
ggtatgcccg gtaaacagat gagtattgat gccgatttga aggccggtat tattgatgcg           480
gatgctgcgc gcgaacggcg aagcgtactg gaaagggaaa gccagcttta cggttccttt           540
gacggtgcga tgaagtttat caaaggtgac gctattgccg gcatcattat tatctttgtg           600
aactttattg gcggtatttc ggtggggatg acccgccatg gtatggattt gtcctccgct           660
ctgtctactt ataccatgct gaccattggt gatggtcttg tcgcccagat ccccgcattg           720
ttgattgcga ttagtgccgg ttttatcgtg actcgcgtaa atggcgatag cgataatatg           780
gggcggaata tcatgacgca gctgttgaac aacccatttg tattggttgt tacggctatt           840
ttgaccattt caatgggaac tctgccggga ttcccgctgc cggtatttgt tattttatcg           900
gtggttttaa gcgtactctt ctattttaaa ttccgtgaag caaaacgtag cgccgccaaa           960

-continued

```
cctaaaaacca gcaaaggcga gcagccgctt agtattgagg aaaaagaagg gtcgtcgttg    1020
ggactgattg gcgatctcga taaagtctct acagagaccg taccgttgat attacttgtg    1080
ccgaagagcc ggcgtgaaga tctggaaaaa gctcaacttg cggagcgtct acgtagtcag    1140
ttctttattg attatggcgt gcgcctgccg gaagtattgt tacgcgatgg cgagggcctg    1200
gacgataaca gcatcgtatt gttgattaat gagatccgtg ttgaacaatt tacggtctat    1260
tttgatttga tgcgagtggt aaattattcc gatgaagtcg tgtcctttgg tattaatcca    1320
acaatccatc agcaaggtag cagtcagtat ttctgggtaa cgcatgaaga gggggagaaa    1380
ctccgggagc ttggctatgt gttgcggaac gcgcttgatg agctttacca ctgtctggcg    1440
gtgaccgtgg cgcgcaacgt caatgaatat ttcggtattc aggaaacaaa acatatgctg    1500
gaccaactgg aagcgaaatt tcctgattta cttaaagaag tgctcagaca tgccacggta    1560
caacgtatat ctgaagtttt gcagcgttta ttaagcgaac gtgtttccgt gcgtaatatg    1620
aaattaatta tggaagcgct cgcattgtgg gcgccaagag aaaaagatgt cattaacctt    1680
gtagagcata ttcgtggagc aatggcgcgt tatatttgtc ataaattcgc caatggcggc    1740
gaattacgag cagtaatggt atctgctgaa gttgaggatg ttattcgcaa agggatccgt    1800
cagacctctg gcagtacctt cctcagcctt gacccggaag cctccgctaa tttgatggat    1860
ctcattacac ttaagttgga tgatttattg attgcacata aagatcttgt cctccttacg    1920
tctgtcgatg tccgtcgatt tattaagaaa                                      1950
```

<210> SEQ ID NO 13
<211> LENGTH: 17
<212> TYPE: DNA
<213> ORGANISM: Artificial Sequence
<220> FEATURE:
<223> OTHER INFORMATION: FRET probe that anneals to Salmonella invA gene
<220> FEATURE:
<221> NAME/KEY: misc_feature
<222> LOCATION: (1)..(1)
<223> OTHER INFORMATION: FAM: 6-carboxyfluorescein chromophore donor
<220> FEATURE:
<221> NAME/KEY: misc_feature
<222> LOCATION: (1)..(7)
<223> OTHER INFORMATION: DNA sequence
<220> FEATURE:
<221> NAME/KEY: misc_feature
<222> LOCATION: (8)..(11)
<223> OTHER INFORMATION: RNA sequence
<220> FEATURE:
<221> NAME/KEY: misc_feature
<222> LOCATION: (12)..(17)
<223> OTHER INFORMATION: DNA sequence
<220> FEATURE:
<221> NAME/KEY: misc_feature
<222> LOCATION: (17)..(17)
<223> OTHER INFORMATION: IaBlkFQ: Iowa Black quencher

<400> SEQUENCE: 13
cggtattcag gaaacaa                                                    17

<210> SEQ ID NO 14
<211> LENGTH: 22
<212> TYPE: DNA
<213> ORGANISM: Artificial Sequence
<220> FEATURE:
<223> OTHER INFORMATION: FRET probe that anneals to Salmonella invA gene
<220> FEATURE:
<221> NAME/KEY: misc_feature
<222> LOCATION: (1)..(1)
<223> OTHER INFORMATION: FAM: 6-carboxyfluorescein chromophore donor
<220> FEATURE:
<221> NAME/KEY: misc_feature
<222> LOCATION: (1)..(9)

```
<223> OTHER INFORMATION: DNA sequence
<220> FEATURE:
<221> NAME/KEY: misc_feature
<222> LOCATION: (10)..(13)
<223> OTHER INFORMATION: RNA sequence
<220> FEATURE:
<221> NAME/KEY: misc_feature
<222> LOCATION: (14)..(22)
<223> OTHER INFORMATION: DNA sequence
<220> FEATURE:
<221> NAME/KEY: misc_feature
<222> LOCATION: (22)..(22)
<223> OTHER INFORMATION: IaBlkFQ: Iowa Black quencher

<400> SEQUENCE: 14
atgtctgagc acutctttaa gt                                            22

<210> SEQ ID NO 15
<211> LENGTH: 24
<212> TYPE: DNA
<213> ORGANISM: Artificial Sequence
<220> FEATURE:
<223> OTHER INFORMATION: primer that anneals to Salmonella invA gene

<400> SEQUENCE: 15
acagtgctcg tttacgacct gaat                                          24

<210> SEQ ID NO 16
<211> LENGTH: 25
<212> TYPE: DNA
<213> ORGANISM: Artificial Sequence
<220> FEATURE:
<223> OTHER INFORMATION: primer that anneals to Salmonella invA gene

<400> SEQUENCE: 16
gattctggta ctaatggtga tgatc                                         25

<210> SEQ ID NO 17
<211> LENGTH: 31
<212> TYPE: DNA
<213> ORGANISM: Artificial Sequence
<220> FEATURE:
<223> OTHER INFORMATION: primer that anneals to Salmonella invA gene

<400> SEQUENCE: 17
gattctggta ctaatggtga tgatcatttc t                                  31

<210> SEQ ID NO 18
<211> LENGTH: 20
<212> TYPE: DNA
<213> ORGANISM: Artificial Sequence
<220> FEATURE:
<223> OTHER INFORMATION: primer that anneals to Salmonella invA gene

<400> SEQUENCE: 18
aaacgttgaa aaactgagga                                               20

<210> SEQ ID NO 19
<211> LENGTH: 24
<212> TYPE: DNA
<213> ORGANISM: Artificial Sequence
<220> FEATURE:
<223> OTHER INFORMATION: primer that anneals to Salmonella invA gene

<400> SEQUENCE: 19
agacggctgg tactgatcga taat                                          24

<210> SEQ ID NO 20
```

-continued

```
<211> LENGTH: 20
<212> TYPE: DNA
<213> ORGANISM: Artificial Sequence
<220> FEATURE:
<223> OTHER INFORMATION: primer that anneals to Salmonella invA gene

<400> SEQUENCE: 20
gccaggctat cgccaataac                                                    20

<210> SEQ ID NO 21
<211> LENGTH: 23
<212> TYPE: DNA
<213> ORGANISM: Artificial Sequence
<220> FEATURE:
<223> OTHER INFORMATION: primer that anneals to Salmonella invA gene

<400> SEQUENCE: 21
tgattctggt actaatggtg atg                                                23

<210> SEQ ID NO 22
<211> LENGTH: 25
<212> TYPE: DNA
<213> ORGANISM: Artificial Sequence
<220> FEATURE:
<223> OTHER INFORMATION: primer that anneals to Salmonella invA gene

<400> SEQUENCE: 22
ctatgttcgt cattccatta cctac                                              25

<210> SEQ ID NO 23
<211> LENGTH: 18
<212> TYPE: DNA
<213> ORGANISM: Artificial Sequence
<220> FEATURE:
<223> OTHER INFORMATION: primer that anneals to Salmonella invA gene

<400> SEQUENCE: 23
ccgtggtcca gtttatcg                                                      18

<210> SEQ ID NO 24
<211> LENGTH: 23
<212> TYPE: DNA
<213> ORGANISM: Artificial Sequence
<220> FEATURE:
<223> OTHER INFORMATION: primer that anneals to Salmonella invA gene

<400> SEQUENCE: 24
aactgaggat tctgtcaatg tag                                                23

<210> SEQ ID NO 25
<211> LENGTH: 26
<212> TYPE: DNA
<213> ORGANISM: Artificial Sequence
<220> FEATURE:
<223> OTHER INFORMATION: primer that anneals to Salmonella invA gene

<400> SEQUENCE: 25
aaaaactgag gattctgtca atgtag                                             26

<210> SEQ ID NO 26
<211> LENGTH: 20
<212> TYPE: DNA
<213> ORGANISM: Artificial Sequence
<220> FEATURE:
<223> OTHER INFORMATION: primer that anneals to Salmonella invA gene

<400> SEQUENCE: 26
```

-continued ggcatccgca tcaataatac                                          20

<210> SEQ ID NO 27
<211> LENGTH: 21
<212> TYPE: DNA
<213> ORGANISM: Artificial Sequence
<220> FEATURE:
<223> OTHER INFORMATION: primer that anneals to Salmonella invA gene

<400> SEQUENCE: 27
gccaggctat cgccaataac g                                        21

<210> SEQ ID NO 28
<211> LENGTH: 19
<212> TYPE: DNA
<213> ORGANISM: Artificial Sequence
<220> FEATURE:
<223> OTHER INFORMATION: probe that anneals to Salmonella invA gene
<220> FEATURE:
<221> NAME/KEY: misc_feature
<222> LOCATION: (1)..(8)
<223> OTHER INFORMATION: DNA sequence
<220> FEATURE:
<221> NAME/KEY: misc_feature
<222> LOCATION: (9)..(11)
<223> OTHER INFORMATION: n = ribothymidine
<220> FEATURE:
<221> NAME/KEY: misc_feature
<222> LOCATION: (12)..(12)
<223> OTHER INFORMATION: RNA sequence
<220> FEATURE:
<221> NAME/KEY: misc_feature
<222> LOCATION: (13)..(19)
<223> OTHER INFORMATION: DNA sequence

<400> SEQUENCE: 28
ctggttgann ncctgatcg                                           19

<210> SEQ ID NO 29
<211> LENGTH: 21
<212> TYPE: DNA
<213> ORGANISM: Artificial Sequence
<220> FEATURE:
<223> OTHER INFORMATION: probe that anneals to Salmonella invA gene
<220> FEATURE:
<221> NAME/KEY: misc_feature
<222> LOCATION: (1)..(9)
<223> OTHER INFORMATION: DNA sequence
<220> FEATURE:
<221> NAME/KEY: misc_feature
<222> LOCATION: (10)..(13)
<223> OTHER INFORMATION: RNA sequence
<220> FEATURE:
<221> NAME/KEY: misc_feature
<222> LOCATION: (14)..(21)
<223> OTHER INFORMATION: DNA sequence

<400> SEQUENCE: 29 cagttttca acgtttcctg c                                         21

<210> SEQ ID NO 30
<211> LENGTH: 19
<212> TYPE: DNA
<213> ORGANISM: Artificial Sequence
<220> FEATURE:
<223> OTHER INFORMATION: probe that anneals to Salmonella invA gene
<220> FEATURE:
<221> NAME/KEY: misc_feature
<222> LOCATION: (1)..(6)
<223> OTHER INFORMATION: DNA sequence
<220> FEATURE:
<221> NAME/KEY: misc_feature
<222> LOCATION: (7)..(11)

```
<223> OTHER INFORMATION: RNA sequence
<220> FEATURE:
<221> NAME/KEY: misc_feature
<222> LOCATION: (12)..(19)
<223> OTHER INFORMATION: DNA sequence

<400> SEQUENCE: 30
cgatcaggaa atcaaccag                                                    19
```

METHOD FOR REAL-TIME DETECTION OF *SALMONELLA* IN FOOD USING A CLEAVABLE CHIMERIC PROBE

CROSS-REFERENCE TO RELATED APPLICATIONS

This application claims priority from U.S. Provisional Patent Application No. 61/312,873, filed on Mar. 11, 2010, the content of which is hereby incorporated by reference in its entirety.

FIELD

The disclosure describes a method and a test kit for the real-time detection of *Salmonella* species in foods and on surfaces.

BACKGROUND

*Salmonella* is a rod-shaped, Gram-negative Enterobacteria. *Salmonella* are closely related to the *Escherichia* genus and are found worldwide in warm- and cold-blooded animals, in humans. They cause illnesses in humans and many animals, such as typhoid fever, paratyphoid fever, and the foodborne illness, salmonellosis. Most persons infected with *Salmonella* develop diarrhea, fever, vomiting, and abdominal cramps 12 to 72 hours after infection. Infection is usually diagnosed by culture of a stool sample. The illness usually lasts 4 to 7 days. Although most people recover without treatment, severe infections can occur. Infants, elderly people, and those with weakened immune systems are more likely than others to develop severe illness. When severe infection occurs, *Salmonella* may spread from the intestines to the bloodstream and then to other body sites and can cause death unless the person is treated promptly with antibiotics.

Currently, there are two recognized *Salmonella* species: *S. enterica* and *S. bongori*, with six main serotypes: *enterica* (I), *salamae* (II), *arizonae* (IIIa), *diarizonae* (IIIb), *houtenae* (IV), and *indica* (VI). The presence of several pathogenicity islands (PAIS) that encode various virulence factors allows *Salmonella* spp. to colonize and infect host organisms. There are two important PAIs, *Salmonella* pathogenicity island 1 and 2 (SPI-1 and SPI-2) that encode two different type III secretion systems for the delivery of effector molecules into the host cell that result in internalization of the bacteria which then leads to systemic spread. *Salmonella bongori* is reptile-specific and is rarely found in human infections. Certain serovars of *Salmonella enterica* are responsible for more serious diseases such as Typhoid fever. *Salmonella* contamination of various foods and surfaces is recognized as a major health hazard by the United States Department of Agriculture Food Safety Inspection Service (FSIS). *Salmonella* is not destroyed by freezing.

Traditionally, *Salmonella* in food and on surfaces was detected by performing classical microbiological assays which are time consuming, labor intensive, insensitive, expensive and difficult to automate. With the advent of DNA amplification technologies, *Salmonella* is now routinely detected by nucleic acid analysis of raw and processed food samples or surface wipe tests. Nucleic acid assays are now adopted by most government agencies as the method of choice to monitor food processing facilities and distribution centers. Nucleic acid analysis permits not only the detection of *Salmonella*, the identification of the serotype but also the tracking of a *Salmonella* outbreak. Such monitoring improves public health and safety by putting hospitals and the medical community on notice and also allows for the rapid identification and isolation of the source of the contamination.

For example, in 2009, the FDA announced they had traced the source of an outbreak of *Salmonella typhimurium* to a plant in Blakely, Ga., owned by Peanut Corporation of America (PCA), and urged people to postpone eating commercially-prepared or manufactured peanut butter-containing products and institutionally-served peanut butter. *Salmonella* was reported to be found in 46 states in the United States in at least 3,862 peanut butter-based products such as crackers, energy bars, and peanut butter cookies from at least 343 food companies. Dog treats were affected as well. At least 691 people in more than 46 states became sick, and the *Salmonella* claimed at least nine lives. Peanut butter and peanut paste manufactured by PCA were distributed to hundreds of firms for use as an ingredient in thousands of different products, such as cookies, crackers, cereal, candy and ice cream, all of which were recalled. Some products were also sold directly to consumers in retail outlets. Containment of a *Salmonella* outbreak therefore presents governmental agencies with a daunting, logistical task.

A prompt and comprehensive response to a *Salmonella* outbreak undoubtedly saves money, widespread illness and even lives. Nevertheless, PCR amplification methods are prone to the detection of false-positives (as described in WO 95/33854) and false-negatives (as described in WO 92/01056, WO 95/00664, WO 92/01056, WO 93/04202). For the foregoing reasons, there is still a unmet need in the art for the accurate and reliable real-time detection of *Salmonella* nucleic acid sequences in test samples.

SUMMARY

In accordance with an embodiment, PCR and CataCleave technologies are combined to design a kit for the real-time detection of *Salmonella* species in foods and on surfaces by targeting the *Salmonella* species specific invasion gene. In accordance with a further aspect, a method is described for monitoring the real-time detection reaction to identify quality control problems using an internal control whose nucleic acid sequences are unrelated to *Salmonella* species.

In one embodiment, a method is described for the real-time detection of *Salmonella* in a sample, comprising the steps of providing a sample to be tested for the presence of a *Salmonella* target DNA, providing a pair of amplification primers that can anneal to the *Salmonella* target DNA, providing a probe comprising a detectable label with DNA and RNA nucleic acid sequences that are substantially complimentary to the *Salmonella* target DNA, amplifying a PCR fragment between the first and second amplification primers in the presence of an amplifying polymerase activity, amplification buffer; a RNase H activity and the probe and under conditions where the RNA sequences within the probe can form a RNA:DNA heteroduplex with the complimentary DNA sequences in the PCR fragment of the *Salmonella* target DNA, and detecting a real-time increase in the emission of a signal from the label on the probe, wherein the increase in signal indicates the presence of the *Salmonella* target DNA in the sample.

In one aspect, the real-time increase in the emission of the signal from the label on the probe results from the RNase H cleavage of the heteroduplex formed between the probe and one of the strands of the PCR fragment.

The *Salmonella* target DNA sequence can comprise the InvA gene.

The DNA and RNA sequences in the probe can be covalently linked to each other. The detectable label on the probe can be a fluorescent label, such as a FRET pair. The amplification buffer can be a HEPES buffer. The probe or PCR fragment can be linked to a solid support. The amplifying polymerase activity can be an activity of a thermostable DNA polymerase and the RNase H activity can be the activity of a thermostable RNase H. The RNase H may be site non-specific or site specific. In an embodiment, the RNase H is a RNase HII. In another embodiment, the RNase HII originated from *Pyrococcus furiosus, Thermus thermophilus, Pyrococcus horikoshi*, or *Thermococus litoralis*. The sample can include a food sample or a sample of a surface wipe. The template nucleic acid with the sample can be treated with Uracil-N-Glycosylase (UNG) that is inactivated prior to PCR amplification to prevent carryover contamination.

In one aspect, the probe has the sequence of SEQ ID NO: 7, 13 or 14.

In another aspect, the pair of amplification primers can be the pair of primers of SEQ ID NOs: 1 and 2, the pair of primers of SEQ ID NOs: 3 and 4 or the pair of primers of SEQ ID NOs: 5 and 6.

In another embodiment, it is disclosed a method for the real-time detection of *Salmonella* in a sample, comprising the steps of providing a sample to be tested for the presence of a *Salmonella* target RNA, providing a pair of reverse and forward amplification primers that can anneal to a *Salmonella* invA target nucleic acid sequence, reverse transcribing *Salmonella* invA target RNA in the presence of a reverse transcriptase activity and the reverse amplification primer to produce a target cDNA sequence, amplifying the target cDNA sequence between the first and second amplification primers in the presence of an amplifying polymerase activity to produce a PCR fragment, providing a probe comprising a detectable label and DNA and RNA nucleic acid sequences that are substantially complimentary to the PCR fragment and an RNase H activity under conditions where the RNA sequences within the probe can form a RNA:DNA heteroduplex with complimentary sequences in the PCR fragment and detecting a real-time increase in the emission of a signal from the label on the probe, wherein the increase in signal indicates the presence of the *Salmonella* target RNA in the sample.

In one aspect, the real-time increase in the emission of the signal from the label on the probe results from the RNase H cleavage of the heteroduplex RNA: DNA formed between the RNA sequences of the probe and the cDNA sequences of the *Salmonella* target RNA.

In one aspect, the pair of amplification primers can be the pair of primers of SEQ ID NOs: 1 and 2, the pair of primers of SEQ ID NOs: 3 and 4 or the pair of primers of SEQ ID NOs: 5 and 6.

In another embodiment, there is disclosed a kit for the real-time detection of *Salmonella* in a sample, comprising a pair of amplification primers that can anneal to a *Salmonella* target DNA sequence, a probe comprising a detectable label and DNA and RNA nucleic acid sequences that are substantially complimentary to the *Salmonella* target DNA sequence and an amplifying polymerase activity, an amplification buffer and a RNase H.

In another embodiment, the disclosure teaches a kit for the real-time detection of *Salmonella* in a sample, comprising reverse transcriptase activity for the reverse transcription of a target *Salmonella* invA RNA sequence to produce a target cDNA sequence, a pair of amplification primers that can anneal to the target cDNA sequence, wherein the pair of amplification primers is selected from the group consisting of the pair of primers of SEQ ID NOs: 1 and 2, the pair of primers of SEQ ID NOs: 3,and 4, and the pair of primers of SEQ ID NOs: 5 and 6, an amplifying activity for the PCR amplification of the target cDNA sequence between the pair of amplification primers to produce a *Salmonella* invA PCR fragment, a probe comprising a detectable label and DNA and RNA nucleic acid sequences that are substantially complimentary to DNA sequences within the PCR fragment; and an RNAse H activity.

The kits may include positive, internal, and negative controls and Uracil-N-Glycosylase (UNG). The *Salmonella* target DNA may include the InvA gene.

In one aspect of the kits, the probe has a structure of DNA sequence-RNA sequence-DNA sequence, and the DNA and RNA sequences of the probe may be covalently linked, the detectable label on the probe can be a fluorescent label. In other embodiment, the probe may be labeled with a FRET pair. The probe or PCR fragment can be linked to a solid support. The amplification buffer can be HEPES. The amplifying polymerase activity can be the activity of a thermostable DNA polymerase and the RNase H activity can be the activity of a thermostable RNase H.

In another aspect of the kits, the probe may include probes having the sequence of SEQ ID NO: 7, 13 or 14 and the pair of amplification primers can be the pair of primers of SEQ ID NOs: 1 and 2, the pair of primers of SEQ ID NOs: 3 and 4 or the pair of primers of SEQ ID NOs: 5 and 6.

The previously described embodiments have many advantages, including the ability to detect *Salmonella* nucleic acid sequences in a sample in real-time. The detection method is fast, accurate and suitable for high throughput applications. Convenient, user-friendly and reliable diagnostic kits are also described for the detection of *Salmonella* in food samples and on surfaces.

DETAILED DESCRIPTION OF THE INVENTION

Figure 1:
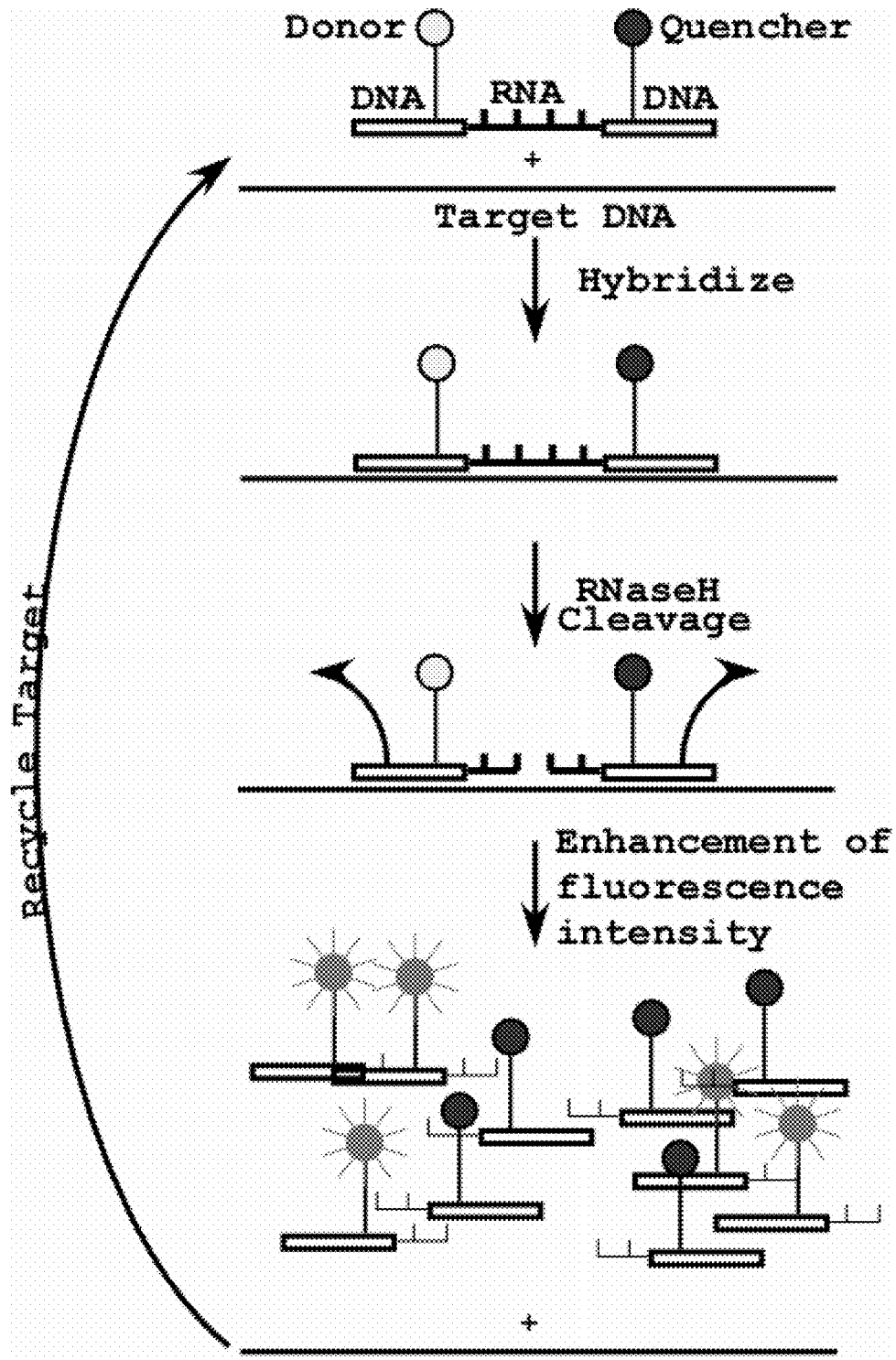
FIG. 1 is a schematic representation of CataCleave probe technology.

The practice of the embodiments described herein employs, unless otherwise indicated, conventional molecular biological techniques within the skill of the art. Such techniques are well known to the skilled worker, and are explained fully in the literature. See, e.g., Ausubel, et al., ed., Current Protocols in Molecular Biology, John Wiley & Sons, Inc., NY, N.Y. (1987-2008), including all supplements; Sambrook, et al., Molecular Cloning: A Laboratory Manual, 2nd Edition, Cold Spring Harbor, N.Y. (1989).

Unless defined otherwise, all technical and scientific terms used herein have the same meaning as is commonly understood by one of skill in the art. The specification also provides definitions of terms to help interpret the disclosure and claims of this application. In the event a definition is not consistent with definitions elsewhere, the definition set forth in this application will control.

As used herein, the term "nucleic acid" refers to an oligonucleotide or polynucleotide, wherein said oligonucleotide or polynucleotide may be modified or may comprise modified bases. Oligonucleotides are single-stranded polymers of nucleotides comprising from 2 to 60 nucleotides. Polynucleotides are polymers of nucleotides comprising two or more nucleotides. Polynucleotides may be either double-stranded DNAs, including annealed oligonucleotides wherein the second strand is an oligonucleotide with the reverse complement sequence of the first oligonucleotide, single-stranded nucleic acid polymers comprising deoxythymidine, single-stranded RNAs, double stranded RNAs or RNA/DNA heteroduplexes. Nucleic acids include, but are not limited to, genomic DNA, cDNA, hnRNA, snRNA, mRNA, rRNA, tRNA, fragmented nucleic acid, nucleic acid obtained from subcellular organelles such as mitochondria or chloroplasts, and nucleic acid obtained from microorganisms or DNA or RNA viruses that may be present on or in a biological sample. Nucleic acids may be composed of a single type of sugar moiety, e.g., as in the case of RNA and DNA, or mixtures of different sugar moieties, e.g., as in the case of RNA/DNA chimeras.

A "target DNA or "target RNA"" or "target nucleic acid," or "target nucleic acid sequence" refers to a nucleic acid that is targeted by DNA amplification. A target nucleic acid sequence serves as a template for amplification in a PCR reaction or reverse transcriptase-PCR reaction. Target nucleic acid sequences may include both naturally occurring and synthetic molecules. Exemplary target nucleic acid sequences include, but are not limited to, genomic DNA or genomic RNA.

As used herein, "label" or "detectable label" can refer to any chemical moiety attached to a nucleotide, nucleotide polymer, or nucleic acid binding factor, wherein the attachment may be covalent or non-covalent. Preferably, the label is detectable and renders said nucleotide or nucleotide polymer detectable to the practitioner of the invention. Detectable labels include luminescent molecules, chemiluminescent molecules, fluorochromes, fluorescent quenching agents, colored molecules, radioisotopes or scintillants. Detectable labels also include any useful linker molecule (such as biotin, avidin, streptavidin, HRP, protein A, protein G, antibodies or fragments thereof, Grb2, polyhistidine, $Ni^{2+}$, FLAG tags, myc tags), heavy metals, enzymes (examples include alkaline phosphatase, peroxidase and luciferase), electron donors/acceptors, acridinium esters, dyes and calorimetric substrates. It is also envisioned that a change in mass may be considered a detectable label, as is the case of surface plasmon resonance detection. The skilled artisan would readily recognize useful detectable labels that are not mentioned above, which may be employed in the operation of the present invention.

Selection of *Salmonella* Target Sequence

A *Salmonella* nucleic acid sequence targeted for DNA amplification is first selected from *Salmonella* nucleic sequences known in the art. As used herein, the term "*Salmonella* target sequence" refers to a DNA or RNA sequence comprising the nucleic acid sequence of a bacterium of the genus *Salmonella*. It includes but is not limited to, species *S. enterica* and *S. bongori* that include, but are not limited to, the subspecies: *enterica* (I), *salamae* (II), *arizonae* (IIIa), *diarizonae* (IIIb), *houtenae* (IV), and *indica* (VI). Exemplary serogroups and serovars of the subspecies *Salmonella enterica* can be found in the U.S. Pat. No. 7,659,381, which is incorporated herein by reference in its entirety.

Exemplary *Salmonella* nucleic acid sequences that may be targeted for amplification according to the present invention are taught by the following publications: Liu W Q et al., "*Salmonella paratyphi* C: genetic divergence from *Salmonella choleraesuis* and pathogenic convergence with *Salmonella typhi*", PLoS One, 2009;4(2):e4510; Thomson N R et al., "Comparative genome analysis of *Salmonella enteritidis* PT4 and *Salmonella gallinarum* 287/91 provides insights into evolutionary and host adaptation pathways," Genome Res, 2008 October ;18(10):1624-37; Encheva V et al., "Proteome analysis of serovars *typhimurium* and Pullorum of *Salmonella enterica* subspecies I.", BMC Microbiol, 2005 Jul. 18 ;5:42; McClelland M et al., "Comparison of genome degradation in Paratyphi A and Typhi, human-restricted serovars of *Salmonella enterica* that cause typhoid", Nat Genet, 2004 December ;36(12):1268-74; Chiu C H et al., "*Salmonella enterica* serotype Choleraesuis: epidemiology, pathogenesis, clinical disease, and treatment," Clin Microbiol Rev, 2004 April ;17(2):311-22; Deng W et al., "Comparative genomics of *Salmonella enterica* serovar Typhi strains Ty2 and CT18," J Bacteriol, 2003 April ;185(7):2330-7; Parkhill J et al., "Complete genome sequence of a multiple drug resistant *Salmonella enterica* serovar Typhi CT18.", Nature, 2001 Oct. 25 ;413(6858):848-52; McClelland M et al., "Complete genome sequence of *Salmonella enterica* serovar *typhimurium* LT2," Nature, 2001 Oct. 25 ;413(6858):852-6, of which contents are incorporated herein by reference. An exemplary nucleotide sequence of the complete 4857432 by genome of *Salmonella enterica* subsp. *enterica* serovar *typhimurium* str. LT2 is available under Genbank Accession No. NC_003197.

In an embodiment, the amplification probe which anneals to the target *Salmonella* invA nucleic acid sequence may be the sequence of SEQ ID NO: 7, 13 or 14.

In another embodiment, the target nucleic acid sequence is the *Salmonella*-specific InvA gene nucleic acid sequence having the following DNA sequence:

SEQ ID NO:12, *Salmonella enterica* InvA gene (GenBank Accession No.: U43272.1):

```
AACAGTGCTCGTTTACGACCTGAATTACTGATTCTGGTACTAATGGT

GATGATCATTTCTATGTTCGTCATTCCATTACCTACCTATCTGGTTG

ATTTCCTGATCGCACTGAATATCGTACTGGCGATATTGGTGTTTATG

GGGTCGTTCTACATTGACAGAATCCTCAGTTTTTCAACGTTTCCTGC

GGTACTGTTAATTACCACGCTCTTTCGTCTGGCATTATCGATCAGTA

CCAGCCGTCTTATCTTGATTGAAGCCGATGCCGGTGAAATTATCGCC
```

-continued

ACGTTCGGGCAATTCGTTATTGGCGATAGCCTGGCGGTGGGTTTTGT

TGTCTTCTCTATTGTCACCGTGGTCCAGTTTATCGTTATTACCAAAG

GTTCAGAACGCGTCGCGGAAGTCGCGGCCCGATTTTCTCTGGATGGT

ATGCCCGGTAAACAGATGAGTATTGATGCCGATTTGAAGGCCGGTAT

TATTGATGCGGATGCTGCGCGCGAACGGCGAAGCGTACTGGAAAGGG

AAAGCCAGCTTTACGGTTCCTTTGACGGTGCGATGAAGTTTATCAAA

GGTGACGCTATTGCCGGCATCATTATTATCTTTGTGAACTTTATTGG

CGGTATTTCGGTGGGGATGACCCGCCATGGTATGGATTTGTCCTCCG

CTCTGTCTACTTATACCATGCTGACCATTGGTGATGGTCTTGTCGCC

CAGATCCCCGCATTGTTGATTGCGATTAGTGCCGGTTTTATCGTGAC

TCGCGTAAATGGCGATAGCGATAATATGGGCGGAATATCATGACGC

AGCTGTTGAACAACCCATTTGTATTGGTTGTTACGGCTATTTTGACC

ATTTCAATGGGAACTCTGCCGGGATTCCCGCTGCCGGTATTTGTTAT

TTTATCGGTGGTTTTAAGCGTACTCTTCTATTTTAAATTCCGTGAAG

CAAAACGTAGCGCCGCCAAACCTAAAACCAGCAAAGGCGAGCAGCCG

CTTAGTATTGAGGAAAAAGAAGGGTCGTCGTTGGGACTGATTGGCGA

TCTCGATAAAGTCTCTACAGAGACCGTACCGTTGATATTACTTGTGC

CGAAGAGCCGGCGTGAAGATCTGGAAAAAGCTCAACTTGCGGAGCGT

CTACGTAGTCAGTTCTTTATTGATTATGGCGTGCGCCTGCCGGAAGT

ATTGTTACGCGATGGCGAGGGCCTGGACGATAACAGCATCGTATTGT

TGATTAATGAGATCCGTGTTGAACAATTTACGGTCTATTTTGATTTG

ATGCGAGTGGTAAATTATTCCGATGAAGTCGTGTCCTTTGGTATTAA

TCCAACAATCCATCAGCAAGGTAGCAGTCAGTATTTCTGGGTAACGC

ATGAAGAGGGGGAGAAACTCCGGGAGCTTGGCTATGTGTTGCGGAAC

GCGCTTGATGAGCTTTACCACTGTCTGGCGGTGACCGTGGCGCGCAA

CGTCAATGAATATTTCGGTATTCAGGAAACAAAACATATGCTGGACC

AACTGGAAGCGAAATTTCCTGATTTACTTAAAGAAGTGCTCAGACAT

GCCACGGTACAACGTATATCTGAAGTTTTGCAGCGTTTATTAAGCGA

ACGTGTTTCCGTGCGTAATATGAAATTAATTATGGAAGCGCTCGCAT

TGTGGGCGCCAAGAGAAAAAGATGTCATTAACCTTGTAGAGCATATT

CGTGGAGCAATGGCGCGTTATATTTGTCATAAATTCGCCAATGGCGG

CGAATTACGAGCAGTAATGGTATCTGCTGAAGTTGAGGATGTTATTC

GCAAAGGGATCCGTCAGACCTCTGGCAGTACCTTCCTCAGCCTTGAC

CCGGAAGCCTCCGCTAATTTGATGGATCTCATTACACTTAAGTTGGA

TGATTTATTGATTGCACATAAAGATCTTGTCCTCCTTACGTCTGTCG

ATGTCCGTCGATTTATTAAGAAA

As used herein, the term "oligonucleotide" is used sometimes interchangeably with "primer" or "polynucleotide." The term "primer" refers to an oligonucleotide that acts as a point of initiation of DNA synthesis in a PCR reaction. A primer is usually about 15 to about 35 nucleotides in length and hybridizes to a region complementary to the target sequence.

In certain embodiments, a pair of amplification primers (i.e., forward primer and reverse primer) can be the pair of primers of SEQ ID NOs: 1 and 2, the pair of primers of SEQ ID NOs: 3 and 4, or the pair of primers of SEQ ID NOs: 5 and 6;

A "primer dimer" is a potential by-product in PCR, that consists of primer molecules that have partially hybridized to each other because of strings of complementary bases in the primers. As a result, the DNA polymerase amplifies the primer dimer, leading to competition for PCR reagents, thus potentially inhibiting amplification of the DNA sequence targeted for PCR amplification. In real-time PCR, primer dimers may interfere with accurate quantification by reducing sensitivity.

Figure 6:
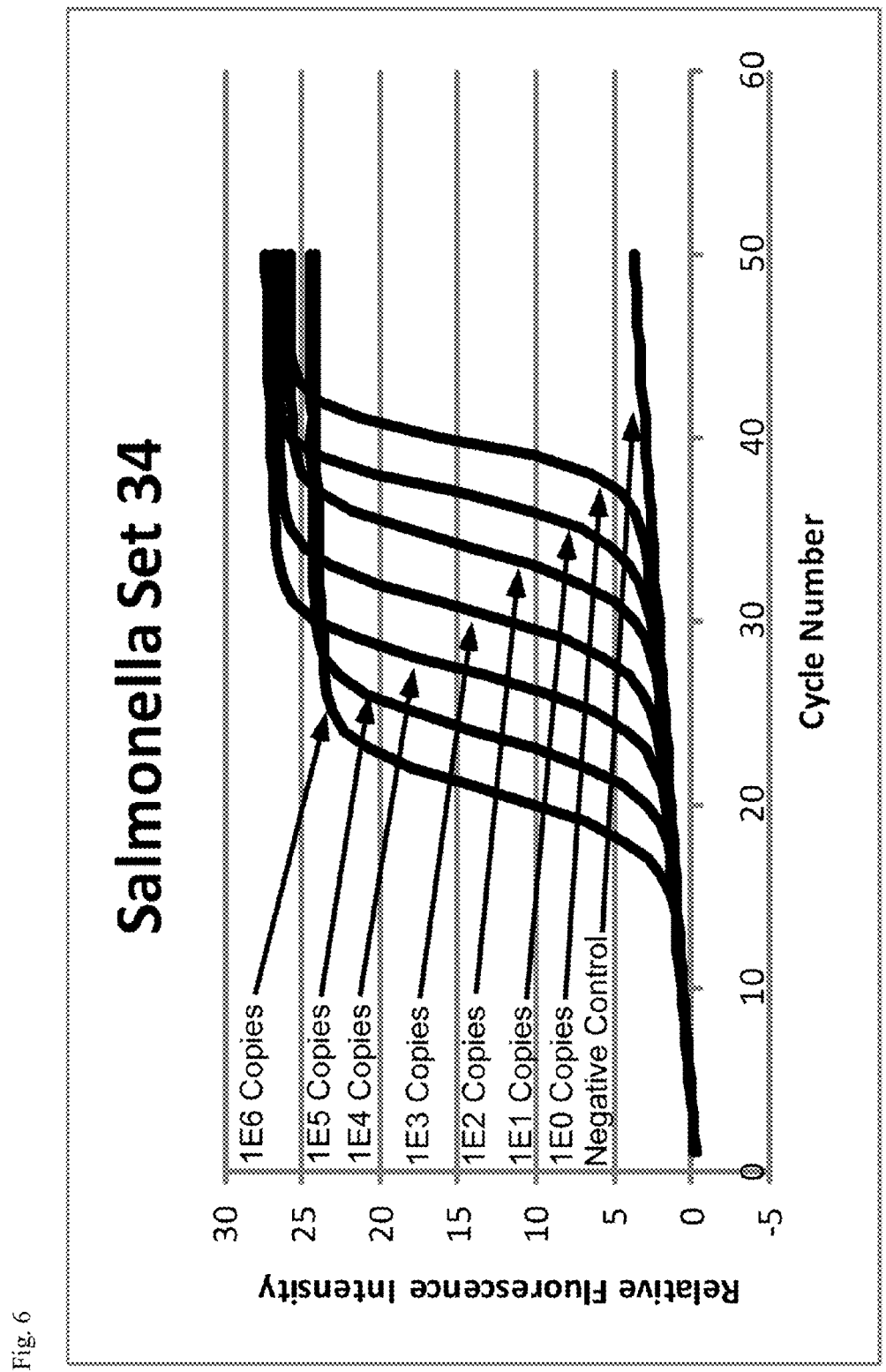
FIG. 6 is the output of a real-time PCR reaction using a CataCleave probe and the amplification primer set 34 having the DNA sequence of SEQ ID NOs: 5 and 6 to detect *Salmonella typhimurium* DNA sequences.
Figure 7:
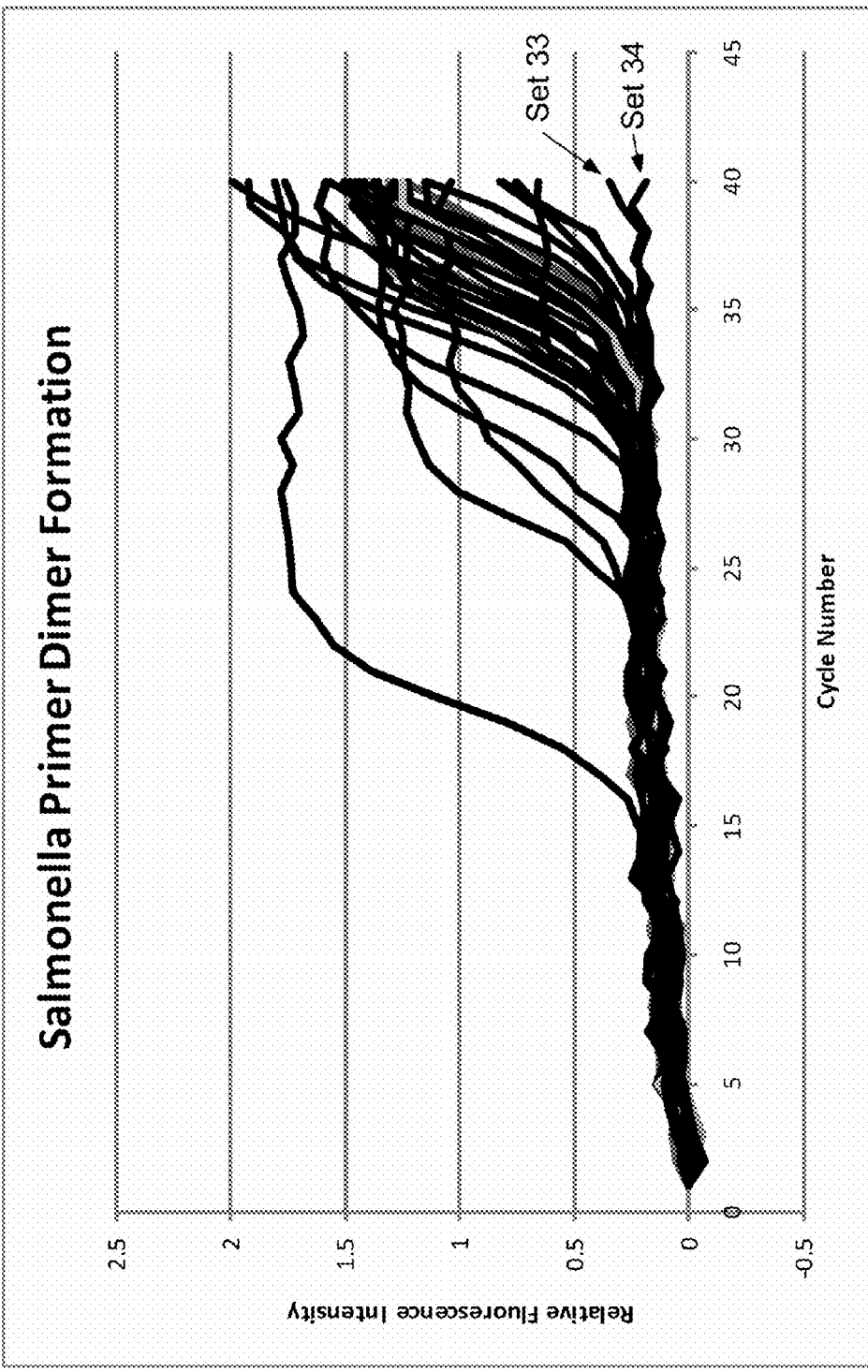
FIG. 7 shows the output of a real-time PCR reaction and the primer dimer formation by different amplification primer pairs.
Figure 8:
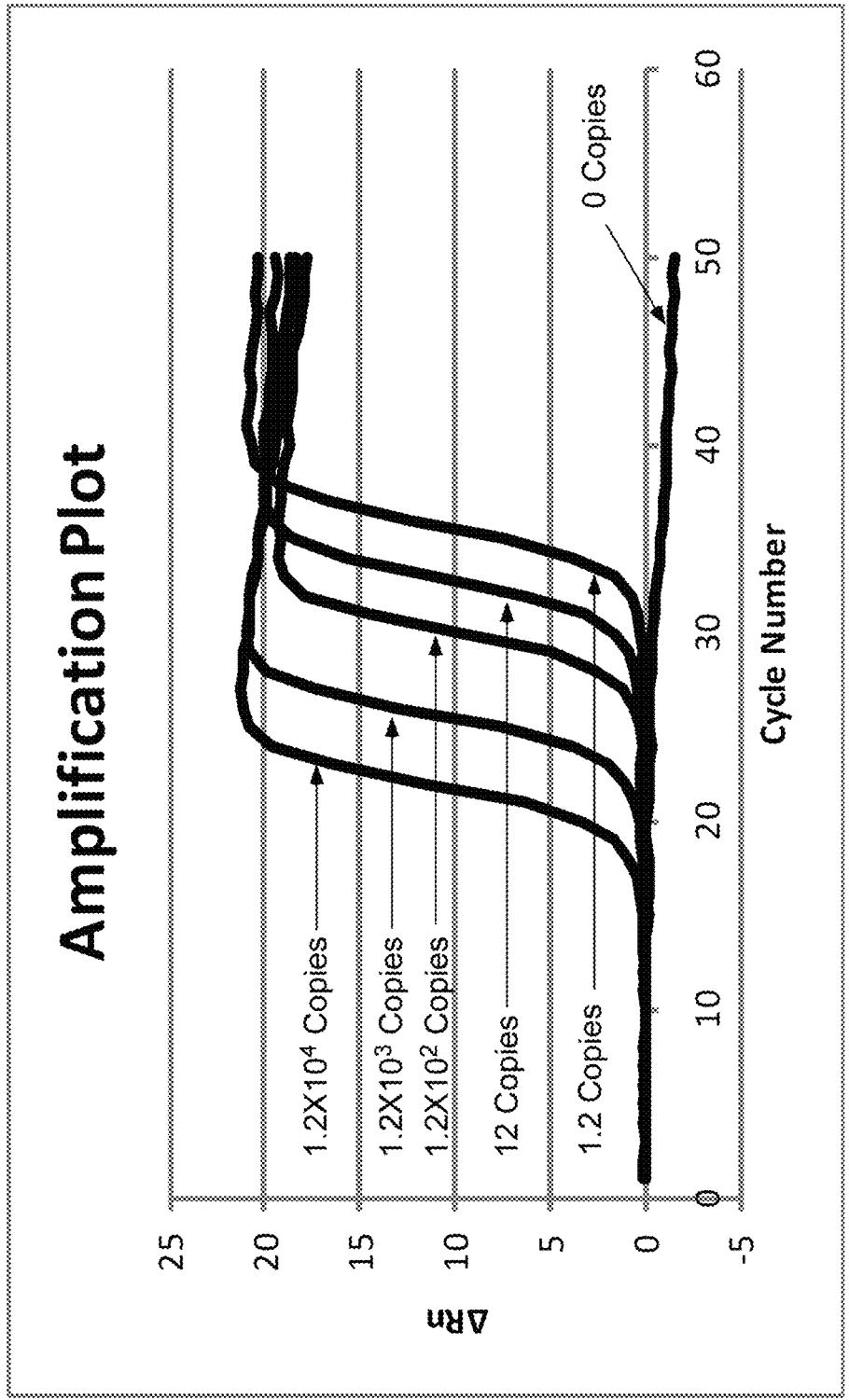
FIG. 8 shows the detection of a single molecule of *Salmonella typhimurium* genomic DNA by real-time PCR using a CataCleave probe and the amplification primer pair of SEQ ID NOs: 1 and 2.
Figure 9:
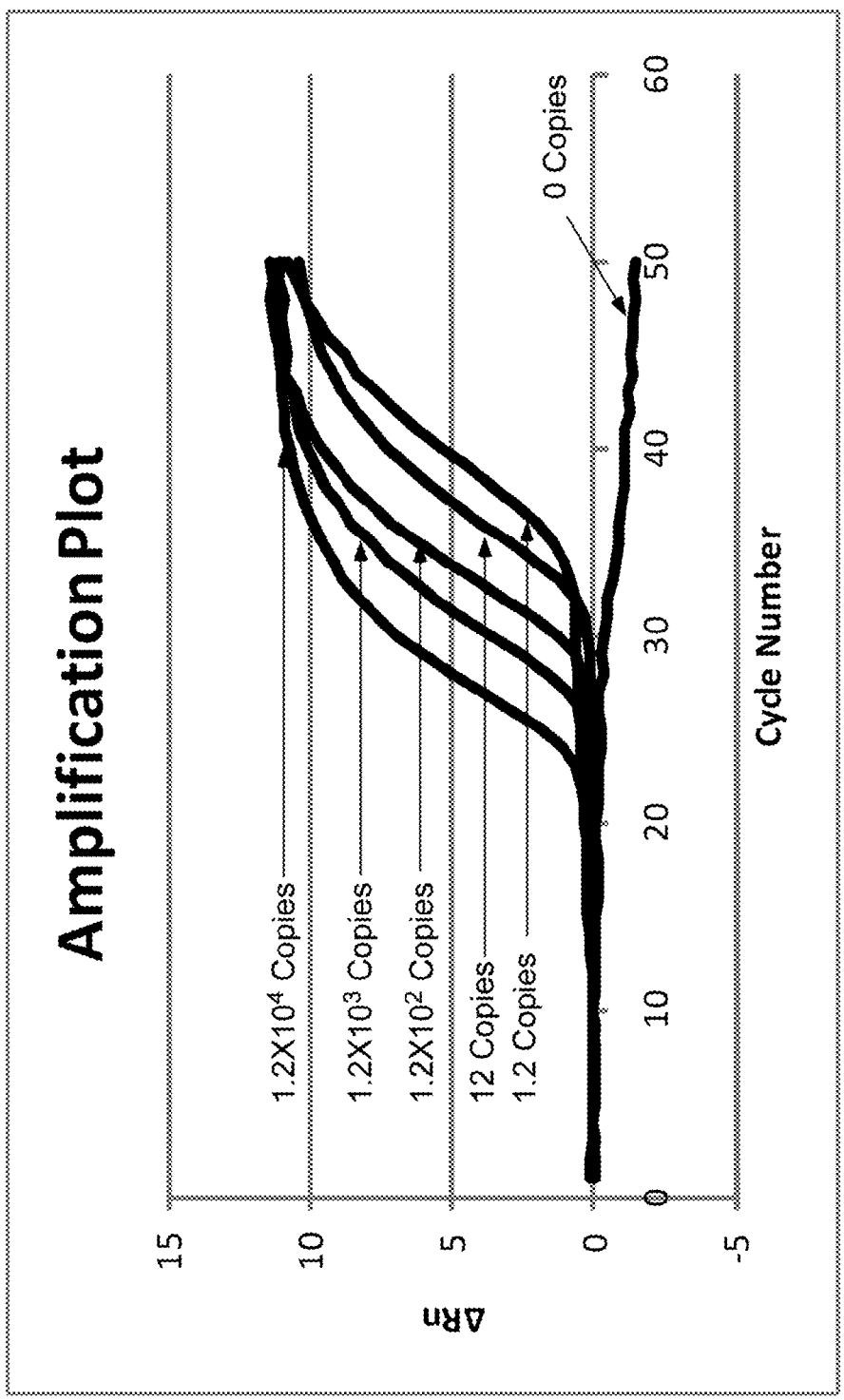
FIG. 9 shows the detection of a single molecule of *Salmonella decatur* genomic DNA by real-time PCR using a Cata-Cleave probe and the amplification primer pair of SEQ ID NOs: 1 and 2.

FIG. 7 shows how primer sequences for the detection of *Salmonella* are screened for the formation of primer-dimer. PCR reactions are performed using pairs of forward and reverse primers in the presence of Sybr Green I. The fluorescence emission intensity of this dye increases when it becomes intercalated into duplex DNA and therefore can serve as a non-specific probe in nucleic acid amplification reactions. The reactions are performed in a suitable reaction buffer described in Example 3 containing 40 nM of forward and reverse primer, thermostable DNA polymerase, and Sybr Green I. The temperature cycling conditions were 95° C. for 5 minutes, followed by 40 cycles of 95° C. for 15 seconds, 55° C. for 15 seconds, and 72° C. for 30 seconds. Real-time data were collected during the 72° C. step. The resulting increase in Sybr Green I fluorescence emission can be detected in real-time using a suitable instrument, such as the Applied Biosystems 7500 Fast Real-Time PCR System or the Biorad CFX96 real-time PCR thermocycler. Primer-dimer formation leads to a characteristic sigmoidal shaped emission profile similar to that seen in the presence of primer-specific template DNA. The figure shows that 32 out of 34 pairs of primers produced significant primer-dimer and were excluded from further analysis. Primer pairs 33 and 34 formed minimal primer-dimer and were used in the assays described in FIGS. 5 and 6.

Oligonucleotides may be synthesized and prepared by any suitable methods (such as chemical synthesis), which are known in the art. Oligonucleotides may also be conveniently available through commercial sources.

The terms "annealing" and "hybridization" are used interchangeably and mean the base-pairing interaction of one nucleic acid with another nucleic acid that results in formation of a duplex, triplex, or other higher-ordered structure. In certain embodiments, the primary interaction is base specific, e.g., A/T and G/C, by Watson/Crick and Hoogsteen-type hydrogen bonding. In certain embodiments, base-stacking and hydrophobic interactions may also contribute to duplex stability.

As used herein, the term "substantially complementary" refers to two nucleic acid strands that are sufficiently complimentary in sequence to anneal and form a stable duplex. The complementarity does not need to be perfect; there may be any number of base pair mismatches, for example, between the two nucleic acids. However, if the number of mismatches is so great that no hybridization can occur under even the least stringent hybridization conditions, the sequence is not a substantially complementary sequence. When two sequences are referred to as "substantially complementary" herein, it means that the sequences are sufficiently complementary to each other to hybridize under the selected reaction conditions. The relationship of nucleic acid complementarity and stringency of hybridization sufficient to achieve specificity is well known in the art. Two substantially complementary strands can be, for example, perfectly complementary or can contain from 1 to many mismatches so long as the hybridization conditions are sufficient to allow, for example discrimination between a pairing sequence and a non-pairing sequence. Accordingly, "substantially complementary" sequences can refer to sequences with base-pair complementarity of 100, 95, 90, 80, 75, 70, 60, 50 percent or less, or any number in between, in a double-stranded region.

A person of skill in the art will know how to design PCR primers flanking a *Salmonella* genomic sequence of interest. Synthesized oligos are typically between 20 and 26 base pairs in length with a melting temperature, $T_M$ of around 55 degrees.

Enrichment for Bacterial Nucleic Acid Sequences in a Test Sample

An exemplary protocol for detecting a target *Salmonella* sequence may include the steps of providing a food sample or surface wipe, mixing the sample or wipe with a growth medium and incubating to increase the number or population of *Salmonella* ("enrichment"), disintegrating *Salmonella* cells ("lysis"), and subjecting the obtained lysate to amplification and detection of target *Salmonella* sequence. Food samples may include, but are not limited to, fish such as salmon, dairy products such as milk, and eggs, poultry, fruit juices, meats such as ground pork, pork, ground beef, or beef, vegetables such as spinach or alfalfa sprouts, or processed nuts such as peanut butter.

The limit of detection (LOD) for food contaminants is described in terms of the number of colony forming units (CFU) that can be detected in either 25 grams of solid or 25 mL of liquid food or on a surface of defined area. By definition, a colony-forming unit is a measure of viable bacterial numbers. Unlike indirect microscopic counts where all cells, dead and living, are counted, CFU measures viable cells. One CFU (one bacterial cell) will grow to form a single colony on an agar plate under permissive conditions. The United States Food Testing Inspection Service defines the minimum LOD as 1 CFU/25 grams of solid food or 25 mL of liquid food or 1 CFU/surface area.

In practice, it is impossible to reproducibly inoculate a food sample or surface with a single CFU and insure that the bacterium survives the enrichment process. This problem is overcome by inoculating the sample at either one or several target levels and analyzing the results using a statistical estimate of the contamination called the Most Probable Number (MPN). As an example, a *Salmonella* culture can be grown to a specific cell density by measuring the absorbance in a spectrophotometer. Ten-fold serial dilutions of the target are plated on agar media and the numbers of viable bacteria are counted. This data is used to construct a standard curve that relates CFU/volume plated to cell density. For the MPN to be meaningful, test samples at several inoculum levels are analyzed. After enrichment and extraction a small volume of sample is removed for real-time analysis. The ultimate goal is to achieve a fractional recovery of between 25% and 75% (i.e. between 25% and 75% of the samples test positive in the assay using -real-time PCR employing a CataCleave probe, which will be explained below). The reason for choosing these fractional recovery percentages is that they convert to MPN values of between 0.3 CFU and 1.375 CFU for 25 gram samples of solid food, 25 mL samples of liquid food, or a defined area for surfaces. These MPN values bracket the required LOD of 1 CFU/sample. With practice, it is possible to estimate the volume of diluted inoculum (based on the standard curve) to achieve these fractional recoveries.

PCR Amplification of *Salmonella* Target Nucleic Acid Sequences

Once the primers are selected and the nucleic acids in a test sample are prepared (see Examples), nucleic acid amplification can be accomplished by a variety of methods, including the polymerase chain reaction (PCR), nucleic acid sequence based amplification (NASBA), ligase chain reaction (LCR), and rolling circle amplification (RCA). The polymerase chain reaction (PCR) is the method most commonly used to amplify specific target DNA sequences.

"Polymerase chain reaction," or "PCR," generally refers to a method for amplification of a desired nucleotide sequence in vitro. The procedure is described in detail in U.S. Pat. Nos. 4,683,202, 4,683,195, 4,800,159, and 4,965,188, the contents of which are hereby incorporated herein in their entirety. Generally, the PCR process consists of introducing a molar excess of two or more extendable oligonucleotide primers to a reaction mixture comprising the desired target sequence(s), where the primers are complementary to opposite strands of the double stranded target sequence. The reaction mixture is subjected to a program of thermal cycling in the presence of a DNA polymerase, resulting in the amplification of the desired target sequence flanked by the DNA primers.

Primers which can be used in the embodiments may have a DNA sequence of SEQ ID NOs 1-6.

Probes which can be used in the embodiments of the instant application (sometimes referred to as "CataCleave probes") may have the following sequences:

```
                                            (SEQ ID NO: 7)
    5'-/FAM/CGATCAGrGrArArATCAACCAG/IABFQ)
```

(wherein, lowercase "r" denotes RNA bases (i.e. rG is riboguanosine)), or

```
                                            (SEQ ID NO: 8)
    5'-/FAM/AGGTAACCrGrArArAACAAGCC/3IABlk_FQ)
```

As used herein, the term "PCR fragment" or "amplicon" refers to a polynucleotide molecule (or collectively the plurality of molecules) produced following the amplification of a particular target nucleic acid. A PCR fragment is typically, but not exclusively, a DNA PCR fragment. A PCR fragment can be single-stranded or double-stranded, or in a mixture thereof in any concentration ratio. A PCR fragment can be 100-500 nucleotides or more in length.

An amplification "buffer" is a compound added to an amplification reaction which modifies the stability, activity, and/or longevity of one or more components of the amplification reaction by regulating the amplification reaction. The buffering agents of the invention are compatible with PCR amplification and RNase H cleavage activity. Examples of buffers include, but are not limited to, HEPES ((4-(2-hydroxyethyl)-1-piperazineethanesulfonic acid), MOPS (3-(N-morpholino)-propanesulfonic acid), and acetate or phosphate containing buffers and the like. In addition, PCR buffers may generally contain up to about 70 mM KCl and about 1.5 mM or higher $MgCl_2$, to about 50-200 µM each of dATP, dCTP, dGTP and dTTP. The buffers of the invention may contain additives to optimize efficient reverse transcriptase-PCR or PCR reactions.

An additive is a compound added to a composition which modifies the stability, activity, and/or longevity of one or more components of the composition. In certain embodiments, the composition is an amplification reaction composition. In certain embodiments, an additive inactivates contaminant enzymes, stabilizes protein folding, and/or decreases aggregation. Exemplary additives that may be included in an amplification reaction include, but are not limited to, betaine, formamide, KCl, CaCl$_2$, MgOAc, MgCl$_2$, NaCl, NH$_4$OAc, NaI, Na(CO$_3$)$_2$, LiCl, MnOAc, NMP, trehalose, demiethylsulfoxide ("DMSO"), glycerol, ethylene glycol, dithiothreitol ("DTT"), pyrophosphatase (including, but not limited to Thermoplasma acidophilum inorganic pyrophosphatase ("TAP")), bovine serum albumin ("BSA"), propylene glycol, glycinamide, CHES, Percoll, aurintricarboxylic acid, Tween 20, Tween 21, Tween 40, Tween 60, Tween 85, Brij 30, NP-40, Triton X-100, CHAPS, CHAPSO, Mackernium, LDAO (N-dodecyl-N,N-dimethylamine-N-oxide), Zwittergent 3-10, Xwittergent 3-14, Xwittergent SB 3-16, Empigen, NDSB-20, T4G32, *E. Coli* SSB, RecA, nicking endonucleases, 7-deazaG, dUTP, anionic detergents, cationic detergents, non-ionic detergents, zwittergent, sterol, osmolytes, cations, and any other chemical, protein, or cofactor that may alter the efficiency of amplification. In certain embodiments, two or more additives are included in an amplification reaction. Additives may be optionally added to improve selectivity of primer annealing provided the additives do not interfere with the activity of RNase H.

As used herein, the term "thermostable," as applied to an enzyme, refers to an enzyme that retains its biological activity at elevated temperatures (e.g., at 55° C. or higher), or retains its biological activity following repeated cycles of heating and cooling. Thermostable polynucleotide polymerases find particular use in PCR amplification reactions.

As used herein, a "thermostable polymerase" is an enzyme that is relatively stable to heat and eliminates the need to add enzyme prior to each PCR cycle. Non-limiting examples of thermostable polymerases may include polymerases isolated from the thermophilic bacteria *Thermus aquaticus* (Taq polymerase), *Thermus thermophilus* (Tth polymerase), *Thermococcus litoralis* (Tli or VENT polymerase), *Pyrococcus furiosus* (Pfu or DEEPVENT polymerase), *Pyrococcus woosii* (Pwo polymerase) and other *Pyrococcus* species, *Bacillus stearothermophilus* (Bst polymerase), *Sulfolobus acidocaldarius* (Sac polymerase), *Thermoplasma acidophilum* (Tac polymerase), *Thermus rubber* (Tru polymerase), *Thermus brockianus* (DYNAZYME polymerase) *Thermotoga neapolitana* (Tne polymerase), *Thermotoga maritime* (Tma) and other species of the *Thermotoga* genus (Tsp polymerase), and *Methanobacterium thermoautotrophicum* (Mth polymerase). The PCR reaction may contain more than one thermostable polymerase enzyme with complementary properties leading to more efficient amplification of target sequences. For example, a nucleotide polymerase with high processivity (the ability to copy large nucleotide segments) may be complemented with another nucleotide polymerase with proofreading capabilities (the ability to correct mistakes during elongation of target nucleic acid sequence), thus creating a PCR reaction that can copy a long target sequence with high fidelity. The thermostable polymerase may be used in its wild type form. Alternatively, the polymerase may be modified to contain a fragment of the enzyme or to contain a mutation that provides beneficial properties to facilitate the PCR reaction. In one embodiment, the thermostable polymerase may be Taq polymerase. Many variants of Taq polymerase with enhanced properties are known and include AmpliTaq, AmpliTaq Stoffel fragment, SuperTaq, SuperTaq plus, LA Taq, LApro Taq, and EX Taq.

Reverse Transcriptase—PCR Amplification of a *Salmonella* RNA Target Nucleic Acid Sequence One of the most widely used techniques to study gene expression exploits first-strand cDNA for mRNA sequence(s) as template for amplification by the PCR. This method, often referred to as reverse transcriptase-PCR, exploits the high sensitivity and specificity of the PCR process and is widely used for detection and quantification of RNA.

The reverse transcriptase-PCR procedure, carried out as either an end-point or real-time assay, involves two separate molecular syntheses: (i) the synthesis of cDNA from an RNA template; and (ii) the replication of the newly synthesized cDNA through PCR amplification. To attempt to address the technical problems often associated with reverse transcriptase-PCR, a number of protocols have been developed taking into account the three basic steps of the procedure: (a) the denaturation of RNA and the hybridization of reverse primer; (b) the synthesis of cDNA; and (c) PCR amplification. In the so called "uncoupled" reverse transcriptase-PCR procedure (e.g., two step reverse transcriptase-PCR), reverse transcription is performed as an independent step using the optimal buffer condition for reverse transcriptase activity. Following cDNA synthesis, the reaction is diluted to decrease MgCl$_2$, and deoxyribonucleoside triphosphate (dNTP) concentrations to conditions optimal for Taq DNA Polymerase activity, and PCR is carried out according to standard conditions (see U.S. Pat. Nos. 4,683,195 and 4,683,202). By contrast, "coupled" reverse transcriptase PCR methods use a common buffer for reverse transcriptase and Taq DNA Polymerase activities. In one version, the annealing of reverse primer is a separate step preceding the addition of enzymes, which are then added to the single reaction vessel. In another version, the reverse transcriptase activity is a component of the thermostable Tth DNA polymerase. Annealing and cDNA synthesis are performed in the presence of Mn$^{2+}$ then PCR is carried out in the presence of Mg$^{2+}$ after the removal of Mn$^{2+}$ by a chelating agent. Finally, the "continuous" method (e.g., one step reverse transcriptase-PCR) integrates the three reverse transcriptase-PCR steps into a single continuous reaction that avoids the opening of the reaction tube for component or enzyme addition. Continuous reverse transcriptase-PCR has been described as a single enzyme system using the reverse transcriptase activity of thermostable Taq DNA Polymerase and Tth polymerase and as a two enzyme system using AMV reverse transcriptase and Taq DNA Polymerase wherein the initial 65° C. RNA denaturation step was omitted.

The first step in real-time, reverse-transcription PCR is to generate the complementary DNA strand using one of the template specific DNA primers. In traditional PCR reactions this product is denatured, the second template specific primer binds to the cDNA, and is extended to form duplex DNA. This product is amplified in subsequent rounds of temperature cycling. To maintain the highest sensitivity it is important that the RNA not be degraded prior to synthesis of cDNA. The presence of RNase H in the reaction buffer will cause unwanted degradation of the RNA:DNA hybrid formed in the first step of the process because it can serve as a substrate for the enzyme. There are two major methods to combat this issue. One is to, physically separate the RNaseH from the rest of the reverse-transcription reaction using a barrier such as wax that will melt during the initial high temperature DNA denaturation step. A second method is to modify the RNase H such that it is inactive at the reverse-transcription temperature, typically 45-55° C. Several methods are known in the art, including reaction of RNase H with an antibody, or reversible chemical modification. For example, a hot start RNAse H activity as used herein can be an RNAse H with a reversible chemical modification produced after reaction of the RNAse H with cis-aconitic anhydride under alkaline conditions. When the modified enzyme is used in a reaction with a Tris based buffer and the temperature is raised to 95° C. the pH of the solution drops and RNase H activity is restored. This method allows for the inclusion of RNase H in the reaction mixture prior to the initiation of reverse transcription.

Additional examples of RNAse H enzymes and hot start RNAse H enzymes that can be employed in the invention are described in U.S. Patent Application No. 2009/0325169 to Walder et al.

One step reverse transcriptase-PCR provides several advantages over uncoupled reverse transcriptase-PCR. One step reverse transcriptase-PCR requires less handling of the reaction mixture reagents and nucleic acid products than uncoupled reverse transcriptase-PCR (e.g., opening of the reaction tube for component or enzyme addition in between the two reaction steps), and is therefore less labor intensive, reducing the required number of person hours. One step reverse transcriptase-PCR also requires less sample, and reduces the risk of contamination. The sensitivity and specificity of one-step reverse transcriptase-PCR has proven well suited for studying expression levels of one to several genes in a given sample or the detection of pathogen RNA. Typically, this procedure has been limited to use of gene-specific primers to initiate cDNA synthesis.

The ability to measure the kinetics of a PCR reaction by real-time detection in combination with these reverse transcriptase-PCR techniques has enabled accurate and precise determination of RNA copy number with high sensitivity. This has become possible by detecting the reverse transcriptase-PCR product through fluorescence monitoring and measurement of PCR product during the amplification process by fluorescent dual-labeled hybridization probe technologies, such as the 5' fluorogenic nuclease assay ("TaqMan") or endonuclease assay ("CataCleave"), discussed below.

Real-Time PCR of a *Salmonella* Target Nucleic Acid Sequence Using a CataCleave Probe Post-amplification amplicon detection is both laborious and time consuming. Real-time methods have been developed to monitor amplification during the PCR process. These methods typically employ fluorescently labeled probes that bind to the newly synthesized DNA or dyes whose fluorescence emission is increased when intercalated into double stranded DNA.

The probes are generally designed so that donor emission is quenched in the absence of target by fluorescence resonance energy transfer (FRET) between two chromophores. The donor chromophore, in its excited state, may transfer energy to an acceptor chromophore when the pair is in close proximity. This transfer is always non-radiative and occurs through dipole-dipole coupling. Any process that sufficiently increases the distance between the chromophores will decrease FRET efficiency such that the donor chromophore emission can be detected radiatively. Common donor chromophores include FAM, TAMRA, VIC, JOE, Cy3, Cy5, and Texas Red. Acceptor chromophores are chosen so that their excitation spectra overlap with the emission spectrum of the donor. An example of such a pair is FAM-TAMRA. There are also non fluorescent acceptors that will quench a wide range of donors. Other examples of appropriate donor-acceptor FRET pairs will be known to those skilled in the art.

Common examples of FRET probes that can be used for real-time detection of PCR include molecular beacons, TaqMan probes (e.g., U.S. Pat. Nos. 5,210,015 and 5,487,972), and CataCleave probes (e.g., U.S. Pat. No. 5,763,181). The molecular beacon is a single stranded oligonucleotide designed so that in the unbound state the probe forms a secondary structure where the donor and acceptor chromophores are in close proximity and donor emission is reduced. At the proper reaction temperature the beacon unfolds and specifically binds to the amplicon. Once unfolded the distance between the donor and acceptor chromophores increases such that FRET is reversed and donor emission can be monitored using specialized instrumentation. TaqMan and CataCleave technologies differ from the molecular beacon in that the FRET probes employed are cleaved such that the donor and acceptor chromophores become sufficiently separated to reverse FRET.

TaqMan technology employs a single stranded oligonucleotide probe that is labeled at the 5' end with a donor chromophore and at the 3' end with an acceptor chromophore. The DNA polymerase used for amplification must contain a 5'->3' exonuclease activity. The TaqMan probe binds to one strand of the amplicon at the same time that the primer binds. As the DNA polymerase extends the primer the polymerase will eventually encounter the bound TaqMan probe. At this time the exonuclease activity of the polymerase will sequentially degrade the TaqMan probe starting at the 5' end. As the probe is digested the mononucleotides comprising the probe are released into the reaction buffer. The donor diffuses away from the acceptor and FRET is reversed. Emission from the donor is monitored to identify probe cleavage. Because of the way TaqMan works a specific amplicon can be detected only once for every cycle of PCR. Extension of the primer through the TaqMan target site generates a double stranded product that prevents further binding of TaqMan probes until the amplicon is denatured in the next PCR cycle.

U.S. Pat. No. 5,763,181, the content of which is incorporated herein by reference, describes another real-time detection method (referred to as "CataCleave"). CataCleave technology differs from TaqMan in that cleavage of the probe is accomplished by a second enzyme that does not have polymerase activity. The CataCleave probe has a sequence within the molecule which is a target of an endonuclease, such as, for example a restriction enzyme or RNAase. In one example, the CataCleave probe has a chimeric structure where the 5' and 3' ends of the probe are constructed of DNA and the cleavage site contains RNA. The DNA sequence portions of the probe are labeled with a FRET pair either at the ends or internally. The PCR reaction includes an RNase H enzyme that will specifically cleave the RNA sequence portion of a RNA-DNA duplex. After cleavage, the two halves of the probe dissociate from the target amplicon at the reaction temperature and diffuse into the reaction buffer. As the donor and acceptors separate FRET is reversed in the same way as the TaqMan probe and donor emission can be monitored. Cleavage and dissociation regenerates a site for further CataCleave binding. In this way it is possible for a single amplicon to serve as a target or multiple rounds of probe cleavage until the primer is extended through the CataCleave probe binding site.

Labeling of a *Salmonella*-Specific CataCleave Probe

The term "probe" comprises a polynucleotide that comprises a specific portion designed to hybridize in a sequence-specific manner with a complementary region of a specific nucleic acid sequence, e.g., a target nucleic acid sequence. In one embodiment, the oligonucleotide probe is in the range of 15-60 nucleotides in length. More preferably, the oligonucleotide probe is in the range of 18-30 nucleotides in length. The precise sequence and length of an oligonucleotide probe of the invention depends in part on the nature of the target polynucleotide to which it binds. The binding location and length may be varied to achieve appropriate annealing and melting properties for a particular embodiment. Guidance for making such design choices can be found in many of the references describing Taq-man assays or CataCleave, described in U.S. Pat. Nos. 5,763,181, 6,787,304, and 7,112,422, the contents of which contents are incorporated herein by reference in their entirety.

As used herein, a "label" or "detectable label" may refer to any label of a CataCleave probe comprising a fluorochrome compound that is attached to the probe by covalent or non-covalent means.

As used herein, "fluorochrome" refers to a fluorescent compound that emits light upon excitation by light of a shorter wavelength than the light that is emitted. The term "fluorescent donor" or "fluorescence donor" refers to a fluorochrome that emits light that is measured in the assays described in the present invention. More specifically, a fluorescent donor provides light that is absorbed by a fluorescence acceptor. The term "fluorescent acceptor" or "fluorescence acceptor" refers to either a second fluorochrome or a quenching molecule that absorbs energy emitted from the fluorescence donor. The second fluorochrome absorbs the energy that is emitted from the fluorescence donor and emits light of longer wavelength than the light emitted by the fluorescence donor. The quenching molecule absorbs energy emitted by the fluorescence donor.

Any luminescent molecule, preferably a fluorochrome and/or fluorescent quencher may be used in the practice of this invention, including, for example, Alexa Fluor 350, Alexa Fluor 430, Alexa Fluor 488, Alexa Fluor 532, Alexa Fluor 546, Alexa Fluor 568, Alexa Fluor 594, Alexa Fluor 633, Alexa Fluor 647, Alexa Fluor 660, Alexa Fluor 680, 7-diethylaminocoumarin-3-carboxylic acid, Fluorescein, Oregon Green 488, Oregon Green 514, Tetramethylrhodamine, Rhodamine X, Texas Red dye, QSY 7, QSY33, Dabcyl, BODIPY FL, BODIPY 630/650, BODIPY 6501665, BODIPY TMR-X, BODIPY TR-X, Dialkylaminocoumarin, Cy5.5, Cy5, Cy3.5, Cy3, DTPA(Eu3+)-AMCA and TTHA ($Eu^{3+}$)AMCA.

In one embodiment, the 3' terminal nucleotide of the oligonucleotide probe is blocked or rendered incapable of extension by a nucleic acid polymerase. Such blocking is conveniently carried out by the attachment of a reporter or quencher molecule to the terminal 3' position of the probe.

In one embodiment, reporter molecules are fluorescent organic dyes derivatized for attachment to the terminal 3' or terminal 5' ends of the probe via a linking moiety. Preferably, quencher molecules are also organic dyes, which may or may not be fluorescent, depending on the embodiment of the invention. For example, in a preferred embodiment of the invention, the quencher molecule is non-fluorescent. Generally whether the quencher molecule is fluorescent or simply releases the transferred energy from the reporter by non-radiative decay, the absorption band of the quencher should substantially overlap the fluorescent emission band of the reporter molecule. Non-fluorescent quencher molecules that absorb energy from excited reporter molecules, but which do not release the energy radiatively, are referred to in the application as chromogenic molecules.

Exemplary reporter-quencher pairs may be selected from xanthene dyes, including fluoresceins, and rhodamine dyes. Many suitable forms of these compounds are widely available commercially with substituents on their phenyl moieties which can be used as the site for bonding or as the bonding functionality for attachment to an oligonucleotide. Another group of fluorescent compounds are the naphthylamines, having an amino group in the alpha or beta position. Included among such naphthylamino compounds are 1-dimethylaminonaphthyl-5-sulfonate, 1-anilino-8-naphthalene sulfonate and 2-p-touidinyl6-naphthalene sulfonate. Other dyes include 3-phenyl-7-isocyanatocoumarin, acridines, such as 9-isothiocyanatoacridine and acridine orange; N-(p-(2-benzoxazolyl)phenyl)maleimide; benzoxadiazoles, stilbenes, pyrenes, and the like.

In one embodiment, reporter and quencher molecules are selected from fluorescein and non-fluorescent quencher dyes.

There are many linking moieties and methodologies for attaching reporter or quencher molecules to the 5' or 3' termini of oligonucleotides, as exemplified by the following references: Eckstein, editor, Oligonucleotides and Analogues: A Practical Approach (IRL Press, Oxford, 1991); Zuckerman et al., Nucleic Acids Research, 15: 5305-5321 (1987) (3' thiol group on oligonucleotide); Sharma et al., Nucleic Acids Research, 19: 3019 (1991) (3' sulthydryl); Giusti et al., PCR Methods and Applications, 2: 223-227 (1993) and Fung et al., U.S. Pat. No. 4,757,141 (5' phosphoamino group via Aminolink. II available from Applied Biosystems, Foster City, Calif.) Stabinsky, U.S. Pat. No. 4,739,044 (3' aminoalkylphosphoryl group); Agrawal et al., Tetrahedron Letters, 31: 1543-1546 (1990) (attachment via phosphoramidate linkages); Sproat et al., Nucleic Acids Research, 15: 4837 (1987) (5' mercapto group); Nelson et al., Nucleic Acids Research, 17: 7187-7194 (1989) (3' amino group); and the like.

Rhodamine and non-fluorescent quencher dyes are also conveniently attached to the 3' end of an oligonucleotide at the beginning of solid phase synthesis, e.g., Woo et al., U.S. Pat. No. 5,231,191; and Hobbs, Jr., U.S. Pat. No. 4,997,928.

Attachment of a *Salmonella*-Specific CataCleave Probe to a Solid Support

In one embodiment of the invention, the oligonucleotide probe can be attached to a solid support. Different probes may be attached to the solid support and may be used to simultaneously detect different target sequences in a sample. Reporter molecules having different fluorescence wavelengths can be used on the different probes, thus enabling hybridization to the different probes to be separately detected.

Examples of preferred types of solid supports for immobilization of the oligonucleotide probe include polystyrene, avidin coated polystyrene beads cellulose, nylon, acrylamide gel and activated dextran, controlled pore glass (CPG), glass plates and highly cross-linked polystyrene. These solid supports are preferred for hybridization and diagnostic studies because of their chemical stability, ease of functionalization and well defined surface area. Solid supports such as controlled pore glass (500 Å, 1000 Å) and non-swelling high cross-linked polystyrene (1000 Å) are particularly preferred in view of their compatibility with oligonucleotide synthesis.

The oligonucleotide probe may be attached to the solid support in a variety of manners. For example, the probe may be attached to the solid support by attachment of the 3' or 5' terminal nucleotide of the probe to the solid support. However, the probe may be attached to the solid support by a linker which serves to distance the probe from the solid support. The linker is most preferably at least 30 atoms in length, more preferably at least 50 atoms in length.

Hybridization of a probe immobilized to a solid support generally requires that the probe be separated from the solid support by at least 30 atoms, more-preferably at least 50 atoms. In order to achieve this separation, the linker generally includes a spacer positioned between the linker and the 3' nucleoside. For oligonucleotide synthesis, the linker arm is usually attached to the 3'-OH of the 3' nucleoside by an ester linkage which can be cleaved with basic reagents to free the oligonucleotide from the solid support.

A wide variety of linkers are known in the art which may be used to attach the oligonucleotide probe to the solid support. The linker may be formed of any compound which does not significantly interfere with the hybridization of the target sequence to the probe attached to the solid support. The linker may be formed of a homopolymeric oligonucleotide which can be readily added on to the linker by automated synthesis. Alternatively, polymers such as fiinctiorialized polyethylene glycol can be used as the linker. Such polymers are preferred over homopolymeric oligonucleotides because they do not significantly interfere with the hybridization of probe to the target oligonucleotide. Polyethylene glycol is particularly preferred because it is commercially available, soluble in both organic and aqueous media, easy to functionalize, and is completely stable under oligonucleotide synthesis and post-synthesis conditions.

The linkages between the solid support, the linker and the probe are preferably not cleaved during removal of base protecting groups under basic conditions at high temperature. Examples of preferred linkages include carbamate and amide linkages. Immobilization of a probe is well known in the art and one skilled in the art may determine the immobilization conditions.

According to one embodiment of the method, the hybridization probe is immobilized on a solid support. The oligonucleotide probe is contacted with a sample of nucleic acids under conditions favorable for hybridization. In an unhybridized state, the fluorescent label is quenched by the quencher. On hybridization to the target, the fluorescent label is separated from the quencher resulting in fluorescence.

Immobilization of the hybridization probe to the solid support also enables the target sequence hybridized to the probe to be readily isolated from the sample. In later steps, the isolated target sequence may be separated from the solid support and processed (e.g., purified, amplified) according to methods well known in the art depending on the particular needs of the researcher.

Real-Time Detection of *Salmonella* Target Nucleic Acid Sequences Using a CataCleave Probe The labeled oligonucleotide probe may be used as a probe for the real-time detection of *Salmonella* target nucleic acid sequence in a sample.

A CataCleave oligonucleotide probe is first synthesized with DNA and RNA sequences that are complimentary to sequences found within a PCR amplicon comprising a selected *Salmonella* target sequence. In one embodiment, the probe is labeled with a FRET pair, for example, a fluorescein molecule at one end of the probe and a non-fluorescent quencher molecule at the other end. Hence, upon hybridization of the probe with the PCR amplicon, a RNA:DNA heteroduplex forms that can be cleaved by an RNase H activity.

RNase H hydrolyzes RNA in RNA-DNA hybrids. This enzyme was first identified in calf thymus but has subsequently been described in a variety of organisms. RNase H activity appears to be ubiquitous in eukaryotes and bacteria. Although RNase H's constitute a family of proteins of varying molecular weight and nucleolytic activity, substrate requirements appear to be similar for the various isotypes. For example, most RNase H's studied to date function as endonucleases and requiring divalent cations (e.g., $Mg^{2+}$, $Mn^{2+}$) to produce cleavage products with 5' phosphate and 3' hydroxyl termini.

RNase HI from *E. coli* is the best-characterized member of the RNase H family. In addition to RNase HI, a second *E. coli* RNase H, RNase HII has been cloned and characterized (Itaya, M., Proc. Natl. Acad. Sci. USA, 1990, 87, 8587-8591). It is comprised of 213 amino acids while RNase HI is 155 amino acids long. *E. coli* RNase HIM displays only 17% homology with *E. coli* RNase HI. An RNase H cloned from *S. typhimurium* differed from *E. coli* RNase HI in only 11 positions and was 155 amino acids in length (Itaya, M. and Kondo K., Nucleic Acids Res., 1991, 19, 4443-4449).

Proteins that display RNase H activity have also been cloned and purified from a number of viruses, other bacteria and yeast (Wintersberger, U. Pharmac. Ther., 1990, 48, 259-280). In many cases, proteins with RNase H activity appear to be fusion proteins in which RNase H is fused to the amino or carboxy end of another enzyme, often a DNA or RNA polymerase. The RNase H domain has been consistently found to be highly homologous to *E. coli* RNase HI, but because the other domains vary substantially, the molecular weights and other characteristics of the fusion proteins vary widely.

In higher eukaryotes two classes of RNase H have been defined based on differences in molecular weight, effects of divalent cations, sensitivity to sulfhydryl agents and immunological cross-reactivity (Busen et al., Eur. J. Biochem., 1977, 74, 203-208). RNase HI enzymes are reported to have molecular weights in the 68-90 kDa range, be activated by either Mn.sup.2+ or Mg.sup.2+ and be insensitive to sulfhydryl agents. In contrast, RNase H II enzymes have been reported to have molecular weights ranging from 31-45 kDa, to require $Mg^{2+}$ to be highly sensitive to sulfhydryl agents and to be inhibited by $Mn^{2+}$ (Busen, W., and Hausen, P., Eur. J. Biochem., 1975, 52, 179-190; Kane, C. M., Biochemistry, 1988, 27, 3187-3196; Busen, W., J. Biol. Chem., 1982, 257, 7106-7108.).

An enzyme with RNase HII characteristics has been purified to near homogeneity from human placenta (Frank et al., Nucleic Acids Res., 1994, 22, 5247-5254). This protein has a molecular weight of approximately 33 kDa and is active in a pH range of 6.5-10, with a pH optimum of 8.5-9. The enzyme requires $Mg^{2+}$ and is inhibited by $Mn^{2+}$ and n-ethyl maleimide. The products of cleavage reactions have 3' hydroxyl and 5' phosphate termini.

According to an embodiment, real-time nucleic acid amplification is performed on a target polynucleotide in the presence of a thermostable nucleic acid polymerase, an RNase H activity, a pair of PCR amplification primers capable of hybridizing to the *Salmonella* target polynucleotide, and the labeled CataCleave oligonucleotide probe. During the real-time PCR reaction, cleavage of the probe by RNase H leads to the separation of the fluorescent donor from the fluorescent quencher and results in the real-time increase in fluorescence of the probe corresponding to the real-time detection of *Salmonella* target DNA sequences in the sample.

In certain embodiments, the real-time nucleic acid amplification permits the real-time detection of a single target DNA molecule in less than about 40 PCR amplification cycles as shown in FIG. 7.

Kits

The disclosure herein also provides for a kit format which comprises a package unit having one or more reagents for the real-time detection of *Salmonella* target nucleic acid sequences in a sample. The kit may also contain one or more of the following items: buffers, instructions, and positive or negative controls. Kits may include containers of reagents mixed together in suitable proportions for performing the methods described herein. Reagent containers preferably contain reagents in unit quantities that obviate measuring steps when performing the subject methods.

Kits may also contain reagents for real-time PCR including, but not limited to, a thermostable polymerase, thermostable RNase H, primers selected to amplify a *Samonella* nucleic acid target sequence and a labeled CataCleave oligonucleotide probe that anneals to the real-time PCR product and allow for the detection of *Salmonella* target nucleic acid sequences according to the methodology described herein.

Kits may comprise reagents for the detection of of two or more *Salmonella* target nucleic acid sequences. In another embodiment, the kit reagents further comprised reagents for the extraction of genomic DNA or RNA from a biological sample. Kit reagents may also include reagents for reverse transcriptase-PCR analysis where applicable.

In certain embodiments, the amplification primer pair has the sequence of SEQ ID NOs 1 and 2 or 3 and 4 or 5 and 6.

In other embodiments, the CataCleave oligonucleotide probe has the sequence of SEQ ID NOs: 7 or 8 or 13 or 14.

Exemplary Real-Time Detection of *Salmonella* InvA Gene Sequences in a Sample

Referring to Example 1, an embodiment of the enrichment of *Salmonella* species in a food sample (solid or liquid) or on a surface. Food samples are placed in a plastic bag and incubated at a temperature that approximates the normal storage temperature for the sample being tested for 24-48 hours. This mimics the handling that the sample would normally receive during commercial processing or in a domestic kitchen and allows for natural die off or growth of bacterial contaminants. For illustrative purposes the salmon in Example 1 were artificially inoculated with *Salmonella paratyphi* B to mimic a contaminated sample. Normally, the sample would be processed as received from the production facility. For surfaces the samples are either 4 inches by 4 inches or I inch by 1 inch. Surface samples are wiped with a sponge of defined dimension hydrated in 10 mL of Dey-Engley broth, for 4×4 inch samples, or swabs moistened in Dey-Engley broth for 1×1 inch samples. The sponges and swabs are placed in individual plastic bags. Surface samples do not undergo the initial storage period of 24-48 hours, After the initial storage period, food samples are further subdivided into either multiple 25 gram or 25 mL portions, depending on the sample matrix. The portions are placed in individual plastic bags prior to enrichment.

Surface and portioned food samples are enriched in 225 mL of trypticase soy broth. Broth is added to each plastic bag, the bags are sealed, and the contents are processed in a stomacher device to distribute the enrichment broth throughout the sample. The samples are then incubated at about 35° C. to about 42° C. for 18-24 hours. During this incubation period, *Salmonella* will multiply in any of the sample bags whose contents were already contaminated. The enrichment insures that the *Salmonella* titer in contaminated samples is high enough so that sufficient nucleic acid can be recovered for analysis.

Referring to Example 2, an embodiment describing the lysis of enriched samples for recovery of nucleic acid. Small portions of sample enrichment are lysed in a Tris-HCl buffered solution containing sodium azide, proteinase K, and the detergent Triton X-100. The proteinase K and Triton X-100 break down the bacterial cell wall so that the nucleic acid is released. The function of the sodium azide is poorly understood, but may act as a reducing agent to increase the effectiveness of the lysis reagents. After lysis, the samples are heated to 95° C. to inactivate the proteinase K.

Figure 2:
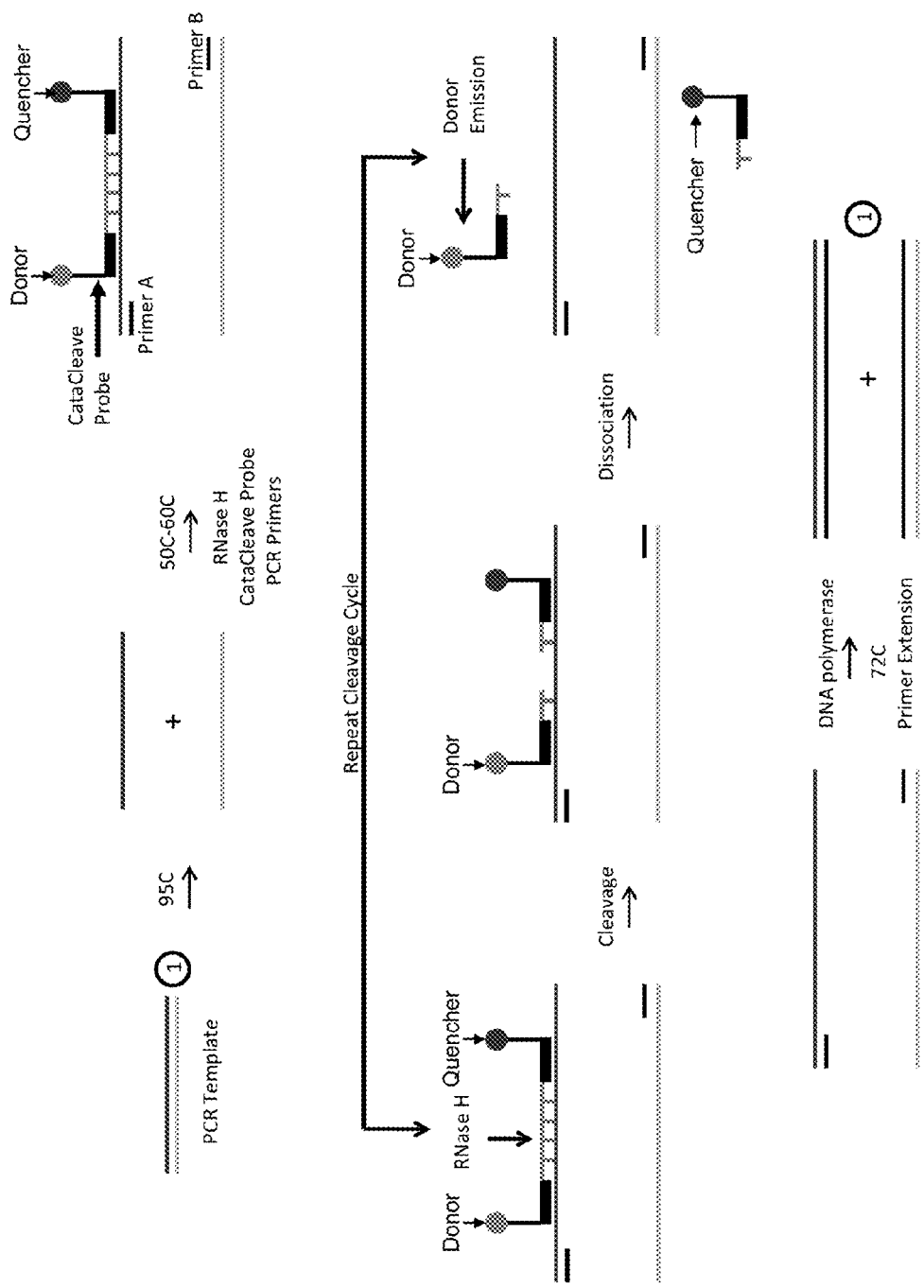
FIG. 2 is a schematic representation of real-time Cata-Cleave probe detection of PCR amplification products.

Referring to FIG. 2, an embodiment of a combined PCR/CataCleave probe detection assay for *Salmonella* species in food and on surfaces is illustrated. PCR primers specific for the amplification of a portion of the *Salmonella* species specific invasion gene having SEQ ID NOs 1 and 2 are combined with a CataCleave probe that can be used for real-time detection of the amplicons. The reaction is performed in a suitable reaction buffer described in Example 3 containing thermostable RNase H, thermostable DNA polymerase, and Uracil-N-Glycosylase (UNG). During the reaction cycle the sample is first incubated at 37 C so that the Uracil-N-Glycosylase can cleave any nucleic acid containing uracil that was carried over from previous assays. This material is a contaminant that will result in false positive detection of *Salmonella*. UNG does not effect the nucleic acid recovered from the bacterial lysis as it does not contain uracil in place of thymidine. After incubation, the nucleic acid recovered from the lysis is denatured at high temperature and the UNG is inactivated. As the temperature is lowered, invasion gene specific primers and CataCleave probe hybridize to any *Salmonella* species-specific amplicon. After hybridization, the CataCleave probe can be cleaved by the action of RNase H, which cleaves the RNA portion of a RNA/DNA duplex. Once cleaved, the probe fragments dissociate from their target and diffuse into the reaction buffer. The CataCleave probe is labeled with a fluorescent donor and quencher so that in the intact state fluorescence from the donor is greatly reduced. Diffusion of the probe fragments increases the distance between the donor and quencher such that the donor fluorescence is no longer attenuated. The resulting increase in donor fluorescence emission can be detected in real-time using a suitable instrument, such as the Applied Biosystems 7500 Fast Real-Time PCR System or the Biorad CFX96 real-time PCR thermocycler. After the probe fragments dissociate from the target, another CataCleave probe can hybridize in the same location and the cleavage reaction is repeated. This cyclic process results in signal amplification as a single amplicon can serve as template for cleavage of multiple CataCleave probes. During this time the gene specific primers are also extended by the DNA polymerase in the presence of nucleoside triphosphates. Once the primers extend over the site for CataCleave probe binding no further cleavage can occur. After extension, the cycle of amplification and detection is completed and the number of amplicons has doubled. These newly synthesized amplicons then serve as template in the next amplification/detection cycle.

Figure 3:
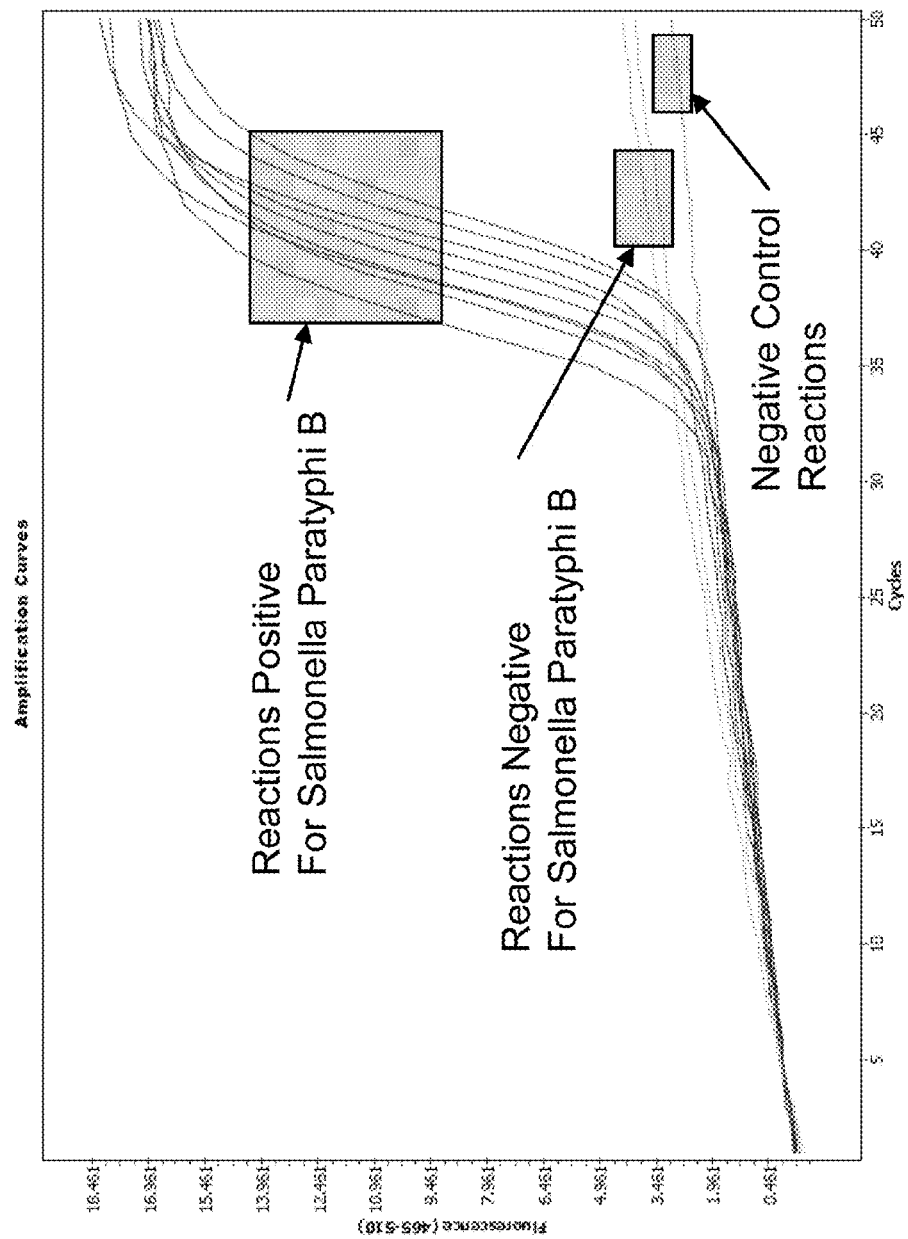
FIG. 3 is the output of a real-time PCR reaction using a CataCleave probe and the amplification primers of SEQ ID NOs: 1 and 2 to detect *Salmonella paratyphi* B contamination in salmon.

Referring to FIG. 3, an embodiment of the result of a real-time PCR CataCleave reaction for salmon artificially inoculated with *Salmonella paratyphi* B. The figure shows that nucleic acid recovered from contaminated salmon samples can serve as a template for the assay. In assays containing a sufficient quantity of DNA template, the fluorescein emission intensity traces have the characteristic shape associated with exponential target amplification. The intensity values eventually plateau as some of the reagents become limiting. Samples that are not contaminated with *Salmonella* do not show any significant increase in fluorescence emission as compared to negative control assays performed using a mock enrichment (where all of the components are known to be sterile).

Figure 4A:
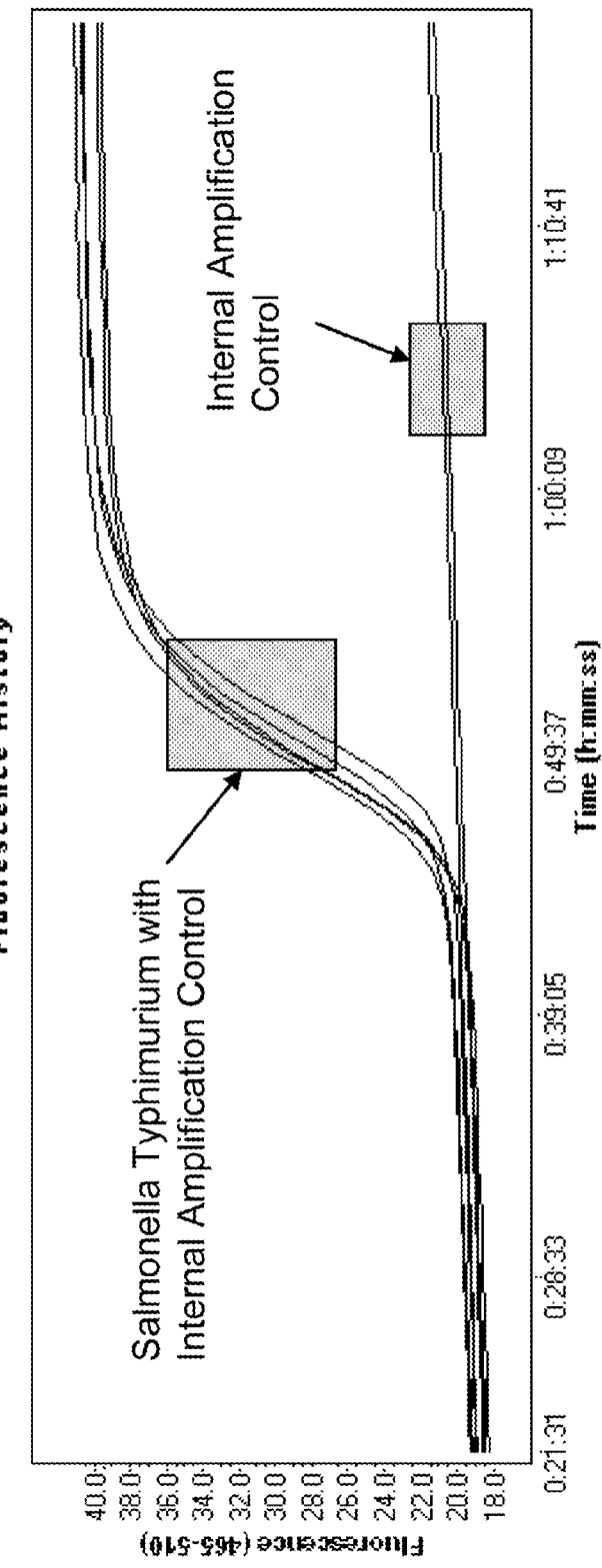
FIG. 4*a* is the output of a real-time PCR reaction using a *Salmonella* specific CataCleave probe to detect *Salmonella typhimurium* contamination in the presence of the internal amplification control plasmid.
Figure 4B:
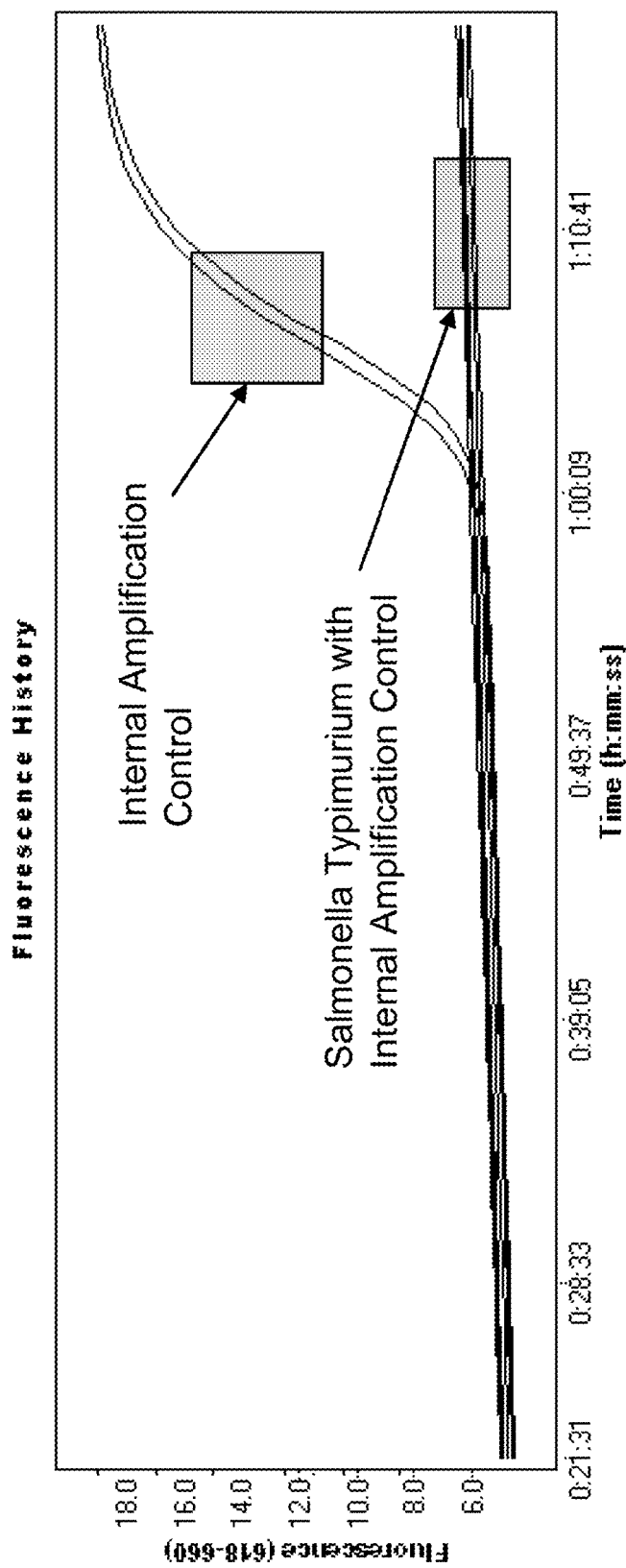
FIG. 4*b* is the output of a real-time PCR reaction using the internal amplification control specific CataCleave probe and internal amplification control plasmid template.

Referring to FIGS. 4*a* and 4*b*, an embodiment of the use of an internal control to validate the components of a real-time PCR CataCleave reaction. The possibility exists that one or more of the reagents used in the real-time assay will have degraded even though they met quality control specifications at the time of kit manufacture. Under these conditions the effected assays will fail and produce false negative results. This situation can be detected by including an internal control in the real-time reaction that is known to produce a positive result in the presence or absence of *Salmonella* species specific template. One example of such an internal control is a plasmid containing a short randomized DNA sequence similar in length to that of the *Salmonella* amplicon, but has different primer and probe binding sites. The included sequence and CataCleave probe must not have any homology with *Salmonella* species or any closely related organism. Example 4 includes this type of internal control. The number of copies of the internal control is limited so as not to interfere with efficient amplification of *Salmonella* Typhimurium.

Figure 5:
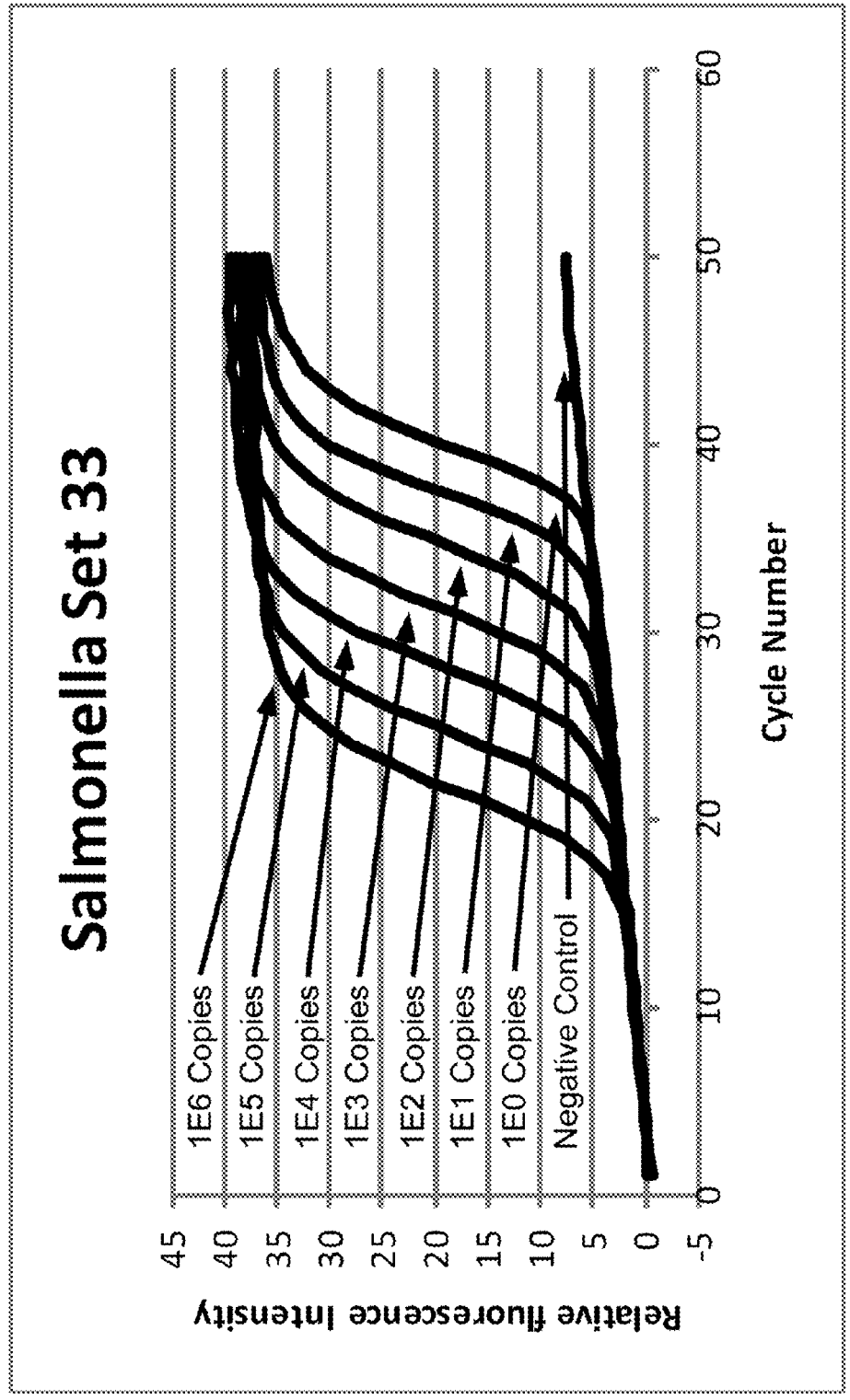
FIG. 5 is the output of a real-time PCR reaction using a CataCleave probe and the amplification primer set 33 having the DNA sequence of SEQ ID NOs: 3 and 4 to detect *Salmonella typhimurium* DNA sequences.

Referring to FIG. 5, an embodiment of a combined PCR/CataCleave probe assay for the detection of from 1 to $10^6$ copies of *Salmonella* genomic DNA is illustrated. PCR primers specific for the amplification of a portion of the *Salmonella* species specific invasion gene having SEQ ID NOs 3 and 4 are combined with a CataCleave probe of SEQ ID NO: 13 that can be used for real-time detection of the amplicons.

Primer and Probe Set 33.

This set amplifies 1409-1564, the probe binds at 1473-1489, (reference Inv gene sequence U43273).

```
Primers:
                                              (SEQ ID NO: 3)
5'-ACG CGC TTG ATG AGC TTT AC (SEQ ID NO: 4)
5'-GTT GTA CCG TGG CAT GTC TG Probe:
                                              (SEQ ID NO: 13)
5'-/FAM/CGG TAT T rCrArGrG AAA CAA/IaBlkFQ/
```

Lowercase "r" denotes RNA in the probe. Donor is FAM, quencher is Iowa Black FQ.

The reaction is performed in a suitable reaction buffer described in Example 3 containing thermostable RNase H, thermostable DNA polymerase, and Uracil-N-Glycosylase (UNG). During the reaction cycle the sample is first incubated at 37° C. so that the Uracil-N-Glycosylase can cleave any nucleic acid containing uracil that was carried over from previous assays. This material is a contaminant that will result in false positive detection of *Salmonella*. UNG does not effect the nucleic acid recovered from the bacterial lysis as it does not contain uracil in place of thymidine. After incubation, the nucleic acid recovered from the lysis is denatured at high temperature and the UNG is inactivated. As the temperature is lowered, invasion gene-specific primers and CataCleave probe hybridize to any *Salmonella* species-specific amplicon. After hybridization, the CataCleave probe can be cleaved by the action of RNase H, which cleaves the RNA portion of a RNA/DNA duplex. Once cleaved, the probe fragments dissociate from their target and diffuse into the reaction buffer. The CataCleave probe is labeled with a fluorescent donor and quencher so that in the intact state fluorescence from the donor is greatly reduced. Diffusion of the probe fragments increases the distance between the donor and quencher such that the donor fluorescence is no longer attenuated. The resulting increase in donor fluorescence emission can be detected in real-time using a suitable instrument, such as the Applied Biosystems 7500 Fast Real-Time PCR System or the Biorad CFX96 real-time PCR thermocycler. After the probe fragments dissociate from the target, another CataCleave probe can hybridize in the same location and the cleavage reaction is repeated. This cyclic process results in signal amplification as a single amplicon can serve as template for cleavage of multiple CataCleave probes. During this time the gene specific primers are also extended by the DNA polymerase in the presence of nucleoside triphosphates. Once the primers extend over the site for CataCleave probe binding no further cleavage can occur. After extension, the cycle of amplification and detection is completed and the number of amplicons has doubled. These newly synthesized amplicons then serve as template in the next amplification/detection cycle.

FIG. 5 shows the primer pair of SEQ ID NOs: 3 and 4 in combination with the Catacleave probe of SEQ ID NO: 13 is able to detect a signal copy of *Salmonella* genomic DNA within 40 or less amplification cycles.

Referring to FIG. 6, an embodiment of a combined PCR/CataCleave probe assay for the detection of from 1 to $10^6$ copies of *Salmonella* genomic DNA is illustrated. PCR primers specific for the amplification of a portion of the *Salmonella* species specific invasion gene having SEQ ID NOs 5 and 6 are combined with a CataCleave probe of SEQ ID NO:14 that can be used for real-time detection of the amplicons.

Primer and Probe Set 34.

This set amplifies 1492-1609, the probe binds at 1530-1551; reference Inv gene sequence U43273).

```
Primers:
                                              (SEQ ID NO: 5)
5'-CAT ATG CTG GAC CAA CTG GA (SEQ ID NO: 6)
5'-CGG AAA CAC GTT CGC TTA AT Probe:
                                              (SEQ ID NO: 14)
5'-/FAM/ATG TCT GAG rCrArCrU TCT TTA AGT /IaBlkFQ/
```

Lowercase "r" denotes RNA in the probe. Donor is FAM, quencher is Iowa Black FQ.

The reaction is performed in a suitable reaction buffer described in Example 3 containing thermostable RNase H, thermostable DNA polymerase, and Uracil-N-Glycosylase (UNG). During the reaction cycle the sample is first incubated at 37° C. so that the Uracil-N-Glycosylase can cleave any nucleic acid containing uracil that was carried over from previous assays. This material is a contaminant that will result in false positive detection of *Salmonella*. UNG does not effect the nucleic acid recovered from the bacterial lysis as it does not contain uracil in place of thymidine. After incubation, the nucleic acid recovered from the lysis is denatured at high temperature and the UNG is inactivated. As the temperature is lowered, invasion gene-specific primers and CataCleave probe hybridize to any *Salmonella* species-specific nucleic acid. After hybridization, the CataCleave probe can be cleaved by the action of RNase H, which cleaves the RNA portion of a RNA/DNA duplex. Once cleaved, the probe fragments dissociate from their target and diffuse into the reaction buffer. The CataCleave probe is labeled with a fluorescent donor and quencher so that in the intact state fluorescence from the donor is greatly reduced. Diffusion of the probe fragments increases the distance between the donor and quencher such that the donor fluorescence is no longer attenuated. The resulting increase in donor fluorescence emission can be detected in real-time using a suitable instrument, such as the Applied Biosystems 7500 Fast Real-Time PCR System or the Biorad CFX96 real-time PCR thermocycler. After the probe fragments dissociate from the target, another CataCleave probe can hybridize in the same location and the cleavage reaction is repeated. This cyclic process results in signal amplification as a single amplicon can serve as template for cleavage of multiple CataCleave probes. During this time the gene specific primers are also extended by the DNA polymerase in the presence of nucleoside triphosphates. Once the primers extend over the site for CataCleave probe binding no further cleavage can occur. After extension, the cycle of amplification and detection is completed and the number of amplicons has doubled. These newly synthesized amplicons then serve as template in the next amplification/detection cycle.

FIG. 6 shows that the primer pair of SEQ ID NOs: 5 and 6 in combination with the CataCleave probe of SEQ ID NO: 14 is able to detect a signal copy of *Salmonella* genomic DNA within 40 or less amplification cycles.

EXAMPLES

The present invention will now be illustrated by the following examples, which are not to be considered limiting in any way.

Example I

Enrichment of *Salmonella Parathyphi* B in Salmon

Salmon was inoculated with *Salmonella Paratyphi* B at a titer of four colony forming units (CFU) per 300 grams. *Salmonella* colonies were inoculated into 5 mL of trypticase soy broth and grown overnight with shaking at 35° C. The cultures were diluted into 1× phosphate buffered saline (PBS) and *Salmonella* titers were determined by plate count assays on trypticase soy agar. Salmon filets were weighed and inoculated with diluted *Salmonella Paratyphi* B in 1× PBS using a pipetteman to distribute the bacteria evenly on the surface of the fish fillet. The treated salmon were placed in a plastic bag and massaged by hand to evenly distribute the inoculum. The bags were sealed and incubated for 48 hours at 4° C.

The samples were subdivided into 25 gram portions using a sterile knife and placed into individual plastic bags. Each portion was resuspended in 225 mL of trypticase soy broth and homogenized for 2 minutes using a stomacher apparatus (Stomacher 400 circulator) at 250 rpm. Samples were incubated at 35° C. for 18-24 hours.

Example 2

Lysis of *Salmonella Paratyhi* B After Enrichment

Portions of the *Salmonella* enrichment (5 uL) were diluted into 45 μL of lysis solution containing 1 mg/mL proteinase K, 0.3125 mg/mL sodium azide, 0.125% Triton X-100, and 12.5 mM Tris-HCl, pH 8.0. The samples were incubated at 55° C. for 15 minutes and then 95° C. for 10 minutes to inactivate the proteinase K and then cooled to 4° C.

Example 3

Real-Time Detection of *Salmonella Paratyphi* B in Salmon

Real-time reactions combined 2 μL of lysate and 23 μL of PCR reaction mix. The PCR reaction mix contained 32 mM HEPES ((4-(2-hydroxyethyl)-1-piperazineethanesulfonic acid)-KOH, pH 7.8, 100 mM potassium acetate, 4 mM magnesium acetate, 0.11% bovine serum albumin, 1% dimethylsulfoxide, 800 μM *Salmonella*-Forward primer, 800 μM *Salmonella*-reverse primer, 200 μM *Salmonella* CataCleave probe, dUTP/NTP mix (80 μM dGTP, dCTP, dATP and 160 μM dUTP), 2.5 Units *Thermus aquaticus* DNA polymerase, 1 Unit *Pyrococcus furiosis* RNase HII, and 0.1 Unit Uracil-N-Glycosylase.

The *Salmonella* Forward and Reverse primers amplify a 180 base pair fragment contained within the *Salmonella* invasion gene.

The sequences of the primers and probes were:

*Salmonella*-Forward primer: 5'- TCGTCATTCCATTACCTACC (SEQ ID NO: 1)

*Salmonella*-Reverse primer: 5'-TACTGATCGATAATGCCAGACGAA (SEQ ID NO: 2)

*Salmonella* CataCleave Probe: 5'-/FAM/CGATCAGrGrArArATCAACCAG/IABFQ) (SEQ ID NO: 7), where lowercase "r" denotes RNA bases (i.e. rG is riboguanosine)

Abbreviations: FAM: 6-Carboxyfluorescein; IABHQ: Iowa Black Hole Quencher for short wavelength emission from Integrated DNA Technologies (Coralville, Iowa)

Reactions were assembled at room temperature and run on a Roche Lightcycler 480 using the following cycling protocol: 37° C. for 10 minutes; 95° C. for 10 minutes; then 50 cycles of amplification; 95° C. for 15 seconds, 60° C. for 20 seconds.

FAM emission was monitored during the 60° C. step. The resulting real-time FAM signals are shown in FIG. 3. The results show that 9 of the 11 samples tested positive for *Salmonella Paratyphi* B contamination. Negative control reactions contained all of the reaction components, except that 2 μL of water was used in place of the lysate. MPN analysis of the data showed that the detection sensitivity was 0.75 CFU/gram.

Example 4

Quality Control Validation of Real-Time PCR Amplification Reaction

*Salmonella typhimurium* was inoculated into trypticase soy broth and grown overnight with shaking at 35° C. to maximum cell density. A portion of the enrichment (5 uL) was diluted into 45 μL of lysis solution containing 1 mg/mL proteinase K, 0.3125 mg/mL sodium azide, 0.125% Triton X-100, and 12.5 mM Tris-HCl, pH 8.0. The samples were incubated at 55° C. for 15 minutes and then 95° C. for 10 minutes to inactivate the proteinase K and then cooled to 4 C.

Real-time reactions combined 2 μL of lysate and 23 μL of PCR reaction mix. The PCR reaction mix contained 32 mM HEPES ((4-(2-hydroxyethyl)-1-piperazineethanesulfonic acid)-KOH, pH 7.8, 100 mM potassium acetate, 4 mM magnesium acetate, 0.11% bovine serum albumin, 1% dimethylsulfoxide, 800 μM *Salmonella*-Forward primer, 800 μM *Salmonella*-Reverse primer, 200 μM *Salmonella* CataCleave probe, 200 μM Internal Amplification Control CataCleave probe, 15 copies of internal amplification control plasmid, dUTP/NTP mix (80 μM dGTP, dCTP, dATP and 160 μM dUTP), 2.5 Units Thermus aquaticus DNA polymerase, 1 Unit *Thermococcus litoralis* RNase HII, and 0.1 Unit Uracil-N-Glycosylase. The internal amplification control is a plasmid that contains a randomized DNA sequence flanked by binding sites for the *Salmonella* Forward and Reverse primers.

The sequences of the primers and probes were:

*Salmonella*-Forward primer:

```
5'- TCGTCATTCCATTACCTACC    (SEQ ID NO: 1)
```

*Salmonella*-Reverse primer:

```
5'-TACTGATCGATAATGCCAGACGAA    (SEQ ID NO: 2)
```

*Salmonella* CataCleave Probe:

```
                                 (SEQ ID NO: 7)
5'-/FAM/CGATCAGrGrArArATCAACCAG/IABFQ/
```

Salmonella Internal Amplification Control-Forward primer:

5'-CTCGCGCGTAGATTGCCATGCGTAGAGC (SEQ ID NO: 9)

Salmonella Internal Amplification Control-Reverse primer:

5'- GTGAACCCACTTGCCTTTGCGTCTTAAT (SEQ ID NO: 10)

Salmonella Internal Amplification Control Probe:

(SEQ ID NO: 11)
5'-/ TYE665/AGGTAACCrGrArArAACAAGCC-/IABFQ/

Lowercase "r" denotes RNA bases (i.e. rG is riboguanosine)

Abbreviations: FAM: 6-Carboxyfluorescein; TYE 665: variant of Cy5 from Integrated DNA Technologies (Coralvile, Iowa); IABFQ: Black Hole Quencher for short wavelength emission from Integrated DNA Technologies (Coralvile, Iowa); IABRQ: Black Hole Quencher for long wavelength emission from Integrated DNA Technologies (Coralvile, Iowa)

Reactions were assembled at room temperature and run on a Roche Lightcycler 480 using the following cycling protocol: 37° C. for 10 minutes, 95° C. for 10 minutes, then 50 cycles of amplification, 95° C. for 15 seconds and finally 60° C. for 20 seconds.

FAM and TYE 665 (in the Cy5 channel) emission was monitored during the 60° C. step. The resulting real-time FAM (*Salmonella* Typhimurium) and TYE 665 (Internal Amplification Control) signals are shown in FIG. 4a and FIG. 4b. The results show the *Salmonella* and internal amplification controls can be detected simultaneously without crosstalk between the channels. Samples that are positive for the presence of *Salmonella* show a characteristic sigmoidal real-time amplification signal in the FAM channel. At the same time the internal control is monitored in the CY5 channel and this signal is also positive for the presence of the internal amplification control plasmid. This information is used to validate that all components of the reaction mixture are within quality control specifications and that data obtained in the FAM channel are valid.

Example 5

Inclusivity of Primers and Probe (1)

By following substantially the same procedures of Example 3, a total of 116 standard *Salmonella* serovars were tested for detection of their target nucleic acid.

In this Example, sixty (60) *Salmonella* serovars were received from Maryland Department of Health and Mental Hygiene were tested for detection using the same primer/probe set as employed in Example 3. For this test, the procedure of Example 3 was modified in that 5 μl of test cell suspension was extracted in 45 μl of lysis buffer (0.3125 mg/ml sodium azide, 12.5 mM Tris-HCl (pH 8.0), 0.25% CHAPS, and 1 mg/ml proteinase K) at 55° C. for 15 minutes followed by 95° C. for 10 minutes. Two microliters of the resulting lysate was used as template. All serovars were efficiently detected. The results are shown below in Table 1.

TABLE 1

| 1 | 2 | 3 | 4 | 5 | 6 | 7 | 8 |
|---|---|---|---|---|---|---|---|
| S. adelaide | berta | S. eastboume | S. invemess | S. lagos | S. minnesda - | S. poona | S. urbana |
| 0010540001 | 0010610001 | 0010700001 | 0010780001 | 0010860001 | 0010940001 | 00/1020001 | 0011090001 |
| 20.17 | 19.09 | 19.13 | 19.19 | 18.64 | 18.99 | 18.88 | 18.87 |
| S. agama | S. blockley | S. gaminara | S. istanbut | S. iika | S. mississippi | S. rechovot | S. virchow |
| 0010550001 | 0010630001 | 0010710001 | 0010790001 | 0010870001 | 0010950001 | 0011030001 | 0011100001 |
| 16.01 | 19.30 | 18.92 | 19.77 | 20.03 | 19.93 | 19.20 | 19.86 |
| S:agbeni | S. braendetup | S. haardt | S. java | S. litchfield | S. muenster | S. san diego | S. virginia |
| 0010560001 | 0010640001 | 0010720001 | 0010800001 | 0010880001 | 0010960001 | 0011040001 | 0011110001 |
| 19:08 | 19.69 | 19.72 | 19.72 | 20.79 | 19.85 | 18.98 | 19.56 |
| Sialachua | S. bredenev | S. hadar | S. javiana | S. lockleaze | S. newington | S. singapore | S. weltevreden |
| 0010570001 | 0010650001 | 001 0730001 | 0010810001 | 0010890001 | 0010970001 | 0011050001 | 001112000/ |
| 2044 | 18.99 | 19.64 | 19.11 | 18.88 | 20.05 | 20.18 | 18.60 |
| S. apapa | S. coeln | S. hartford | S. johanneslxi | S. manhattan | S. norwich | S. tallahassee | |
| 0019580001 | 0010660001 | 0010740001 | 0010820001 | 0010900001 | 0010980001 | 0011060001 | |
| 19.50 | 17.72 | 18.56 | 19.77 | 19.69 | 18.68 | 18.73 | |
| S. bardo | S. cotham | S. hato | S. kentucky | S. mbandaka | S. ohio | S. telelkebir | |
| 0010590001 | 0:00670001 | 0010750001 | 0010830001 | 0010910001 | 0010990001 | 0011070001 | |
| 18.45 | 18.78 | 18.63 | 18.65 | 18.60 | 20.14 | 18.72 | |
| S. bareilly | S. denver | S. havana | S. kiambu | S. meleagridis | S. oranienburg | tennessee | |
| 0010600001 | 0010680001 | 0010760001 | 0010840001 | 0010920001 | 0011000001 | 0011080001 | |
| 18.33 | 18.88 | 18.86 | 18.81 | 19.63 | 18.96 | 19.31 | |
| S. beaudesert | S. durham | S. hvittingfoss | S. kottbus | S. mendoza | S. oslo | S. typhimurium var copenhagen 0010490003 18.36 | |
| 0010610001 | 0010690001 | 0010770001 | 00/0850001 | 0010930001 | 0011010001 | | |
| 19.08 | 18.89 | 18.90 | 18.95 | 18.49 | 19.83 | | |

In Table 1, the first line of each cell is the name of *Salmonella* strain (serovars), the second line is strain or accession #, and the third line is $C_p$.

Example 6

Inclusivity of Primers and Probe

By following substantially the same procedures of Example 5, fifty-four (54) *Salmonella* serovars purchased from the American Type Culture Collection (ATCC) at Manassas, Va. (USA) were tested for detection using the same primer/probe set as employed in Example 3. All serovars were efficiently detected. The results are shown below in Table 2.

TABLE 2

| 1 | 2 | 3 | 4 | 5 | 6 | 7 |
|---|---|---|---|---|---|---|
| *Abtxtusequi* 0010010001 1848 | *Choleraesuis* 0010090001 16.89 | *Duisburg* 0010160001 16.50 | *Indiana* 0010240001 17.63 | *Panama* 0010320001 '16.58 | *salamae* 0010400001 20.38 | *Typhi* 0010470001 17.83 |
| *Agpna* 0010020001 16.76 | *Choleraesuis* 0010090002 | *Emek* 001017000 1 | *indica* 001.0250001 17.74 | *Paratyphi* A 0010330001 17.11 | *salamae* 0010410001 18.71 | *Typhi* 0010480002 16.96 |
| *Anaium* 0010030001 18.09 .- ,- | *Decatur* 0010100001 19.19 | *Enteritidis* 0010180001 17.24 | *indica* 0010250001 17.55 | *Paratyphi* 13 0010340001 17.48 | *Schwarzengrund* 0010420001 15,93 | *Typhimurium* 0010490001 17,22 |
| *arizonae* 0010040001 17.49 | *Derby* 0010110001 16.66 | *Gallinarum* 0010190001 16.94 | *Infantis* 0010270001 18.53 | *Paratyphi* C 0010350001 16.51 | *Seftenberg* 0010430001 17.24 | *Typhimurium* 0010490002 19.90 |
| *arizanae* 0010050001 16.68 | *diarizonae* 0010120001 16.82 | *Haifa* 0010200001 16.03 | *Miami* 0010280001 16.96 | *Pullorum* 0010360001 17.29 | *Sendai* 0010440001 17.57 | *Typhisuis* 0010440001 17.93 |
| *bongo(*' 0010060001 19.05 | *diarizonae* 0010130001 17.58 | *Heidelberg* 0010210001 19.52 | *Montevideo* 0010290001 r.24 | *Reading* 0010370001 16.63 | *Stanley* 0010450001 16.19 | VII 0010510001 18.01 |
| *bongori* 0010070001 19.53 | *diarizonae* 0010140001. 15.97 | *Houtenae* 0010220001 19.89 | *Muenchen* 0010300001 18.76 | *Rubislaw* 0010380001 17.23 | *Stanleyville* 0010460001 17.50 | VII 0010520001 17.78 |
| *Srandenberg* 0010080001 18.87 | *Dublin* 0010150001 N | *houtenae* 0010230001 17.67 | *Newport* 0010310001' 17.45 | *Saintpaul* 0010390001 16.14 | *Thompson* 0010470001 18.25 | *Wien* 0010530001 16.96 |

In Table 2, the first line of each cell is the name of *Salmonella* strain (serovera serovars), the second line is strain or accession #, and the third line is $C_p$.

Example 7

Testing of Food Samples

By following substantially the same procedures of Example 5, various food samples were inoculated with respective of *Salmonella* serovars shown in Table 3, and tested for detecting the *Salmonella* serovars. The results are shown below in Table 3. In Table 3, it is noted that a fractional positive ratio obtained from an inoculation level is considered valid by AOAC International (Gaithersburg, Md., USA).

TABLE 3

| Food type | *Salmonella* serovar | *Salmonella* concentration (CFU/25 gram or milliliter) | Positive ratio |
|---|---|---|---|
| Milk | *S. Dublin* | 0.8 | 60% |
| Ground pork | *S. Choleraesuis* | 1.5 | 80% |
| Ground beef | *S. Newport* | 2.3 | 60% |
| Chicken | *S. Heidelberg* | 1.5 | 40% |
| Pork | *S. Derby* | 0.7 | 50% |
| Orange juice | *S. Muenchen* | 0.9 | 58% |
| Peanut butter | *S. Agona* | 1.4 | 75% |
| Alfalfa sprouts | *S. Typhimurium* | 0.5 | 40% |
| Eggs | *S. Enteritidis* | 0.3 | 25% |
| Salmon | *S. Paratyphi* B | 0.75 | 82% |

Example 8

Comparison of InvA Gene Primer Pairs

InvA gene primers were selected from the following publications:

Hoorfar J. et al., J. Clin. Micro. 38 (2000), pp. 3429-3435

(1) Salmonella-F1:
5'-TCG TCA TTC CAT TAC CTA CC   (SEQ ID NO: 1)

(2) Salmonella-R:
5'-AAA CGT TGA AAA ACT GAG GA   (SEQ ID NO: 18)

Trafny E A et al., Lett. Appl. Micro. 43 (2006), pp. 673-679.

(1) Sal-invF:
5'-ACA GTG CTC GTT TAC GAC CTG AAT (SEQ ID NO: 15)

(2) Sal-invR:
5'-AGA CGG CTG GTA CTG ATC GAT AAT (SEQ ID NO: 19)

Fey A. et al. App. Env. Micro. 70 (2004), pp. 3618-3623.

(1) Sal-InvA2-F1:
(SEQ ID NO: 16)
5' GAT TCT GGT ACT AAT GGT GAT GAT C (2) Sal-InvA2-R1:
(SEQ ID NO: 20)
5' GCC AGG CTA TCG CCA ATA AC (3) Sal-InvA2-F2:
(SEQ ID NO: 17)
5'- GAT TCT GGT ACT AAT GGT GAT GAT CAT TTC T (4) Sal-InvA2-R2:
(SEQ ID NO: 27)
5'- GCC AGG CTA TCG CCA ATA ACG

Modifications were made to some of these primers to generate new unique ones:

(1) InvA-S1:
(SEQ ID NO: 21)
5' TGA TTC TGG TAC TAA TGG TGA TG (2) InvA-S2:
(SEQ ID NO: 22)
5' CTA TGT TCG TCA TTC CAT TAC CTA C

-continued

```
(3) InvA-S3:
                                        (SEQ ID NO: 23)
5' CCG TGG TCC AGT TTA TCG (4) InvA-A1:
                                        (SEQ ID NO: 24)
5' AAC TGA GGA TTC TGT CAA TGT AG (5) InvA-A2:
                                        (SEQ ID NO: 25)
5' AAA AAC TGA GGA TTC TGT CAA TGT AG (6) InvA-A3:
                                        (SEQ ID NO: 26)
5' GGC ATC CGC ATC AAT AAT AC (7) Sal-InvR2:
                                        (SEQ ID NO: 2)
5' TAC TGA TCG ATA ATG CCA GAC GAA
```

InvA gene candidate primers:

| Primer No. | SEQ ID NO. | NAME | Sequence (5'→3') |
|---|---|---|---|
| 1 | 15 | Sal-invF | ACA GTG CTC GTT TAC GAC CTG AAT |
| 2 | 16 | Sal-InvA2-F1 | GAT TCT GGT ACT AAT GGT GAT GAT C |
| 3 | 17 | Sal-InvA2-F2 | GAT TCT GGT ACT AAT GGT GAT GAT CAT TTC T |
| 4 | 1 | Salmonella-F1 | TCG TCA TTC CAT TAC CTA CC |
| 5 | 18 | Salmonella-R | AAA CGT TGA AAA ACT GAG GA |
| 6 | 19 | Sal-invR | AGA CGG CTG GTA CTG ATC GAT AAT |
| 7 | 20 | Sal-InvA2-R1 | GCC AGG CTA TCG CCA ATA AC |
| 8 | 21 | InvA-S1 | TGA TTC TGG TAC TAA TGG TGA TG |
| 9 | 22 | InvA-S2 | CTA TGT TCG TCA TTC CAT TAC CTA C |
| 10 | 23 | InvA-S3 | CCG TGG TCC AGT TTA TCG |
| 11 | 24 | InvA-A1 | AAC TGA GGA TTC TGT CAA TGT AG |
| 12 | 25 | InvA-A2 | AAA AAC TGA GGA TTC TGT CAA TGT AG |
| 13 | 26 | InvA-A3 | GGC ATC CGC ATC AAT AAT AC |
| 14 | 27 | Sal-invA2-R2 | TGA TCG ATA ATG CCA GAC GAA |
| 15 | 2 | Sal-InvR2 | TAC TGA TCG ATA ATG CCA GAC GAA |

Figure 10:
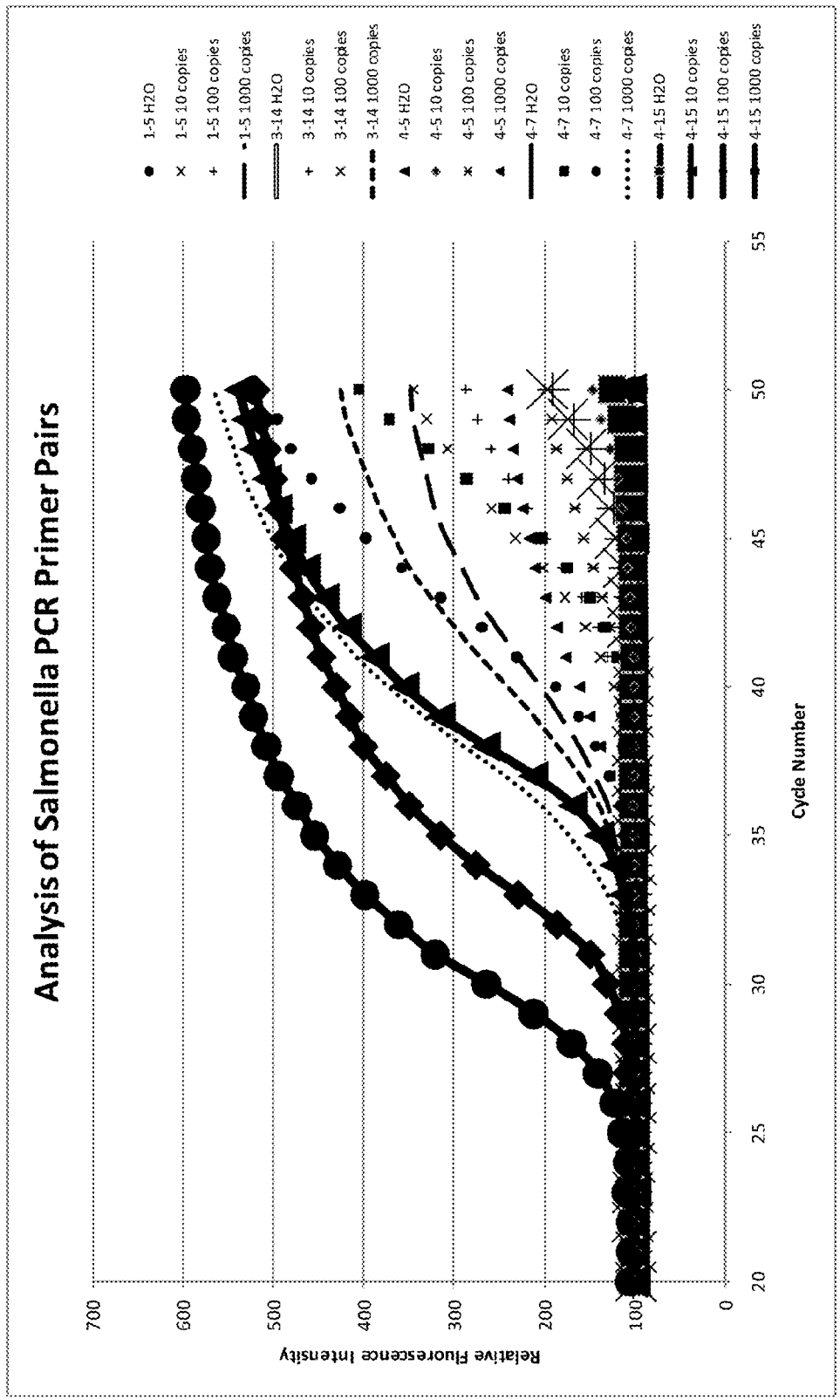
FIG. 10 depicts a comparison of the detection sensitivity of eight pairs of *Salmonella* InvA gene primers using Cata-Cleave real-time PCR.

All 15 of these primers were screened in a matrix to determine *Salmonella* detection sensitivity and for production of primer-dimer (amplicons that result from primers that also act as template for each other). After analysis, eight pairs were found to be capable of detecting between 10 and 1000 copies of target without forming appreciable primer-dimer. These pairs were primer numbers 1-5, 1-7, 3-14, 4-5, 4-7, 8-5, 9-5, and 4-15. Representative data for some of these primer pairs is plotted in FIG. 10.

The results show that, in comparison to the other primer pairs, primer pair 4-15 (corresponding to SEQ ID NO: 1 and 2; thick black lines) exhibits much better performance as the Cp values at each concentration are many cycles lower than the corresponding values for the same concentration using the other primer pairs.

Example 9

Comparison of *Salmonella* InvA Gene Catacleave Probes

Three different probes were synthesized and tested for efficacy.

```
Inv-CC-Probe 1:
5' CTG GTT GArT rTrTrC CTG ATC G    (SEQ ID NO: 28)

Inv-CC-Probe 2:
5' CGA TCA GrGrA rArAT CAA CCA G    (SEQ ID NO: 30)

Inv-CC-Probe 3:
5' CAG TTT TTC rArArC rGTT TCC TGC  (SEQ ID NO: 29)
```

Figure 11:
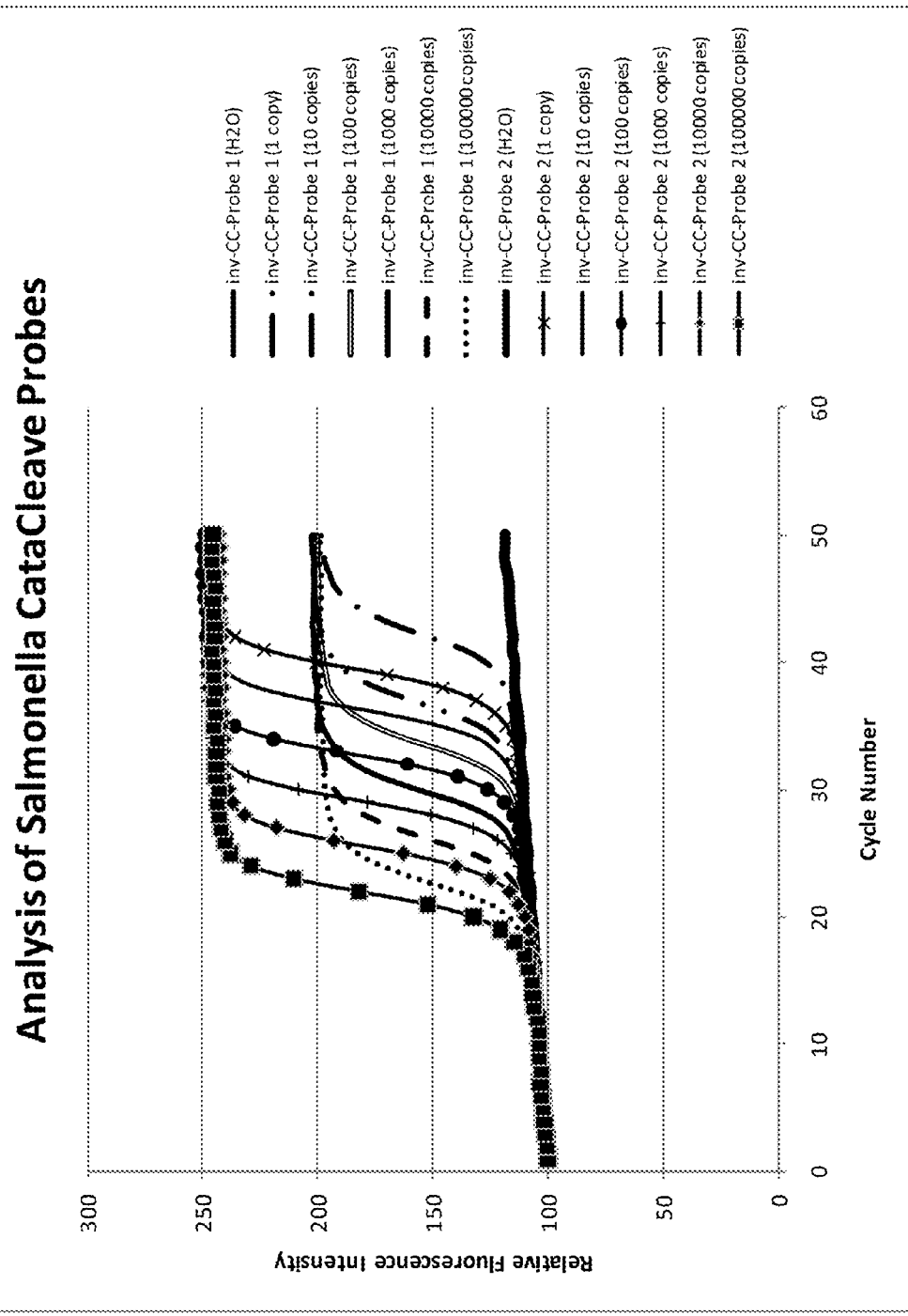
FIG. 11 depicts a comparison of the efficacy of two different CataCleave probes in the real-time PCR detection of *Salmonella* invA DNA sequences.
Figure 12:
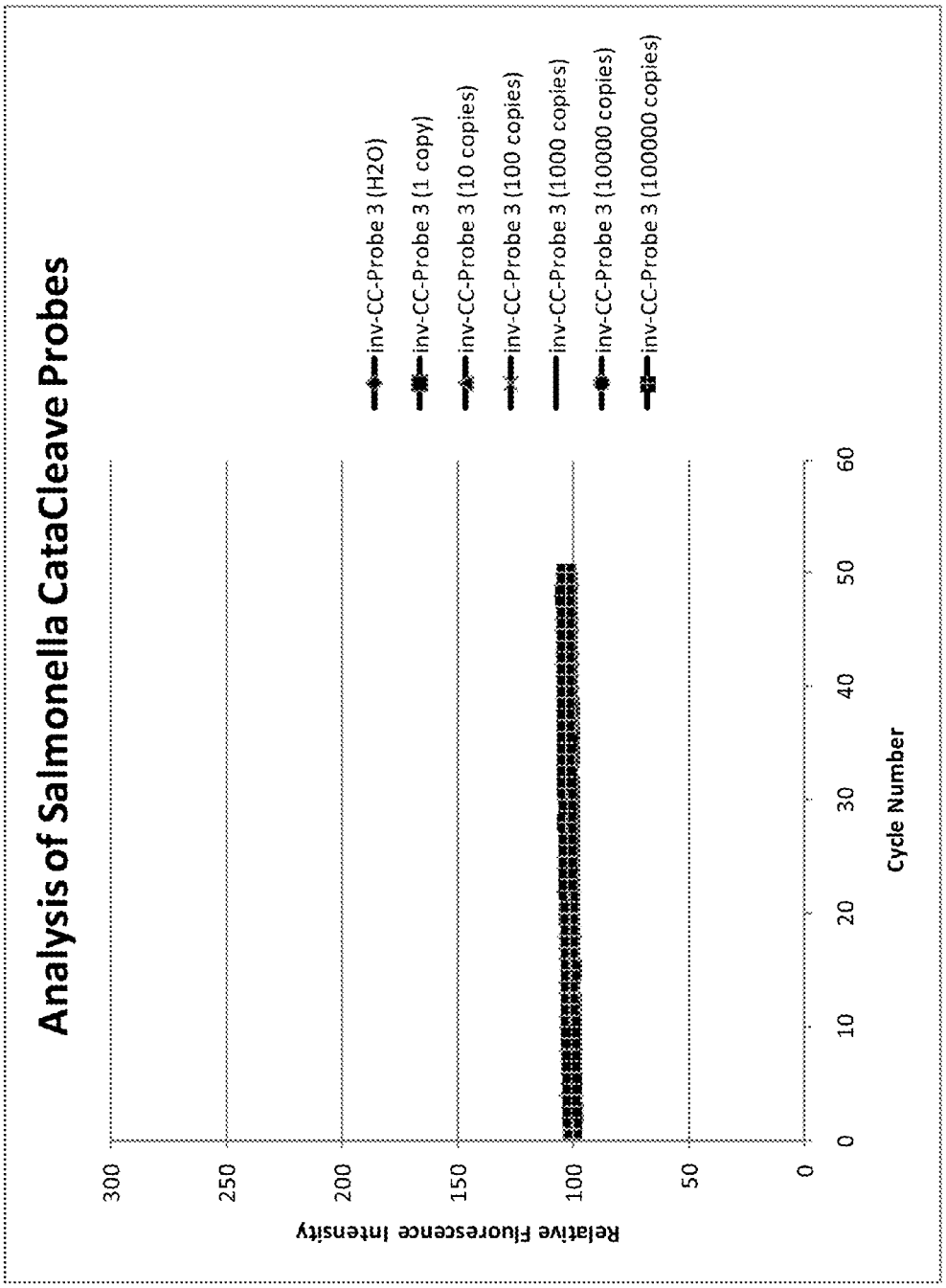
FIG. 12 depicts the efficacy of another probe (CataCleave inv-CC-Probe 3) in the CataCleave real-time PCR detection of from 1 to 100000 copies of *Salmonella* invA gene DNA.

The results are shown in FIG. 11 (Inv-CC-Probe 1 and 2) and FIG. 12 (Inv-CC-probe 3). In comparing probes 1, 2 and 3 the results show that probe 2 has demonstrably better performance than probe 1 both in terms of decreased Cp value, and dynamic range. Probe 3 could not be cleaved in the assay as shown in FIG. 12. These results show that Inv-CC-Probe 2 according to an embodiment of the application shows a greater efficacy over the comparative probes.

Any patent, patent application, publication, or other disclosure material identified in the specification is hereby incorporated by reference herein in its entirety. Any material, or portion thereof, that is said to be incorporated by reference herein, but which conflicts with existing definitions, statements, or other disclosure material set forth herein is only incorporated to the extent that no conflict arises between that incorporated material and the present disclosure material.

What is claimed is:

1. A method for the real-time detection of *Salmonella* in a sample, comprising the steps of:
   a) providing a sample to be tested for the presence of a *Salmonella* invA gene target DNA;
   b) providing a pair of amplification primers that can anneal to the *Salmonella* invA gene target DNA, wherein the pair of amplification primers is the pair of primers of SEQ ID NOs: 1 and 2;
   c) providing a probe comprising a detectable label and DNA and RNA nucleic acid sequences that are substantially complementary to the *Salmonella* target DNA;
   d) amplifying a PCR fragment between the first and second amplification primers in the presence of an amplifying polymerase activity, amplification buffer; an RNAse H activity and the probe and under conditions where the RNA sequences within the probe can form a RNA:DNA heteroduplex with the complementary DNA sequences in the PCR fragment of the *Salmonella* target DNA; and
   e) detecting a real-time increase in the emission of a signal from the label on the probe, wherein the increase in signal indicates the presence of the *Salmonella* target DNA in the sample.

2. The method of claim 1, wherein the real-time increase in the emission of the signal from the label on the probe results from the RNAse H cleavage of the heteroduplex formed between the probe and one of the strands of the PCR fragment.

3. The method of claim 1, wherein the DNA and RNA sequences of the probe are covalently linked.

4. The method of claim 1, wherein the detectable label on the probe is a fluorescent label.

5. The method of claim 1, wherein the probe is labeled with a FRET pair.

6. The method of claim 1, wherein the amplification buffer further comprises a Tris-acetate buffer.

7. The method of claim 1, wherein the PCR fragment is linked to a solid support.

8. The method of claim 1, wherein the amplifying polymerase activity is an activity of a thermostable DNA polymerase.

9. The method of claim 1, wherein the RNAse H activity is the activity of a thermostable RNAse H.

10. The method of claim 1, wherein the RNAse H activity is a hot start RNAse H activity.

11. The method of claim 1, wherein the sample comprises a food sample.

12. The method of claim 1, wherein the sample comprises a surface wipe sample.

13. The method of claim 1, wherein the nucleic acid within the sample is pre-treated with uracil-N-glycosylase.

14. The method of claim 13, wherein the uracil-N-glycosylase is inactivated prior to PCR amplification.

15. The method of claim 1, wherein the probe comprises the sequence of SEQ ID NO: 7.

16. A method for the real-time detection of *Salmonella* in a sample, comprising the steps of:
   a) providing a sample to be tested for the presence of a *Salmonella* invA target RNA;
   b) providing a pair of forward and reverse amplification primers that can anneal to the *Salmonella* invA target nucleic acid sequence, wherein the pair of amplification primers is the pair of primers of SEQ ID NOs: 1 and 2;
   c) providing a probe comprising a detectable label and DNA and RNA nucleic acid sequences that are substantially complementary to the cDNA of the *Salmonella* target RNA;
   d) reverse transcribing the *Salmonella* invA target RNA in the presence of a reverse transcriptase activity and the reverse amplification primer to produce a target cDNA sequence;
   e) amplifying a PCR fragment between the forward and reverse amplification primers in the presence of the target cDNA sequence, an amplifying polymerase activity, an amplification buffer; an RNAse H activity and the probe under conditions where the RNA sequences within the probe can form a RNA:DNA heteroduplex with complementary sequences in the PCR fragment; and
   f) detecting a real-time increase in the emission of a signal from the label on the probe, wherein the increase in signal indicates the presence of the *Salmonella* target RNA in the sample.

17. The method of claim 16, wherein the real-time increase in the emission of the signal from the label on the probe results from the RNAse H cleavage of the RNA:DNA heteroduplex formed between the RNA sequences of the probe and the cDNA sequences of the *Salmonella* target RNA.

18. The method of claim 16, wherein the DNA and RNA sequences of the probe are covalently linked.

19. The method of claim 16, wherein the detectable label on the probe is a fluorescent label.

20. The method of claim 16, wherein the probe is labeled with a FRET pair.

21. The method of claim 16, wherein the amplification buffer comprises a Tris-acetate buffer.

22. The method of claim 16, wherein the PCR fragment is linked to a solid support.

23. The method of claim 16, wherein the amplifying polymerase activity is an activity of a thermostable DNA polymerase.

24. The method of claim 16, wherein the RNAse H activity is the activity of a thermostable RNAse H.

25. The method of claim 16, wherein the RNAse H activity is a hot start RNAse H activity.

26. The method of claim 16, wherein the sample comprises a food sample.

27. The method of claim 16, wherein the sample comprises a surface wipe sample.

28. The method of claim 16, wherein the nucleic acid within the sample is pre-treated with uracil-N-glycosylase.

29. The method of claim 28, wherein the uracil-N-glycosylase is inactivated prior to PCR amplification.

30. The method of claim 16, wherein the probe comprises the sequence of SEQ ID NO: 7.

31. A kit for the real-time detection of *Salmonella* in a sample, comprising:
    a) a pair of amplification primers that can anneal to a *Salmonella* invA target DNA sequence, wherein the pair of amplification primers is the pair of primers of SEQ ID NOs: 1 and 2;
    b) a probe comprising a detectable label and DNA and RNA nucleic acid sequences that are substantially complementary to the *Salmonella* invA target DNA sequence;
    c) an amplifying polymerase activity, and
    d) an RNAse H activity.

32. The kit of claim 31, further comprising positive internal and negative controls.

33. The kit of claim 31, further comprising uracil-N-glycosylase.

34. The kit of claim 31, wherein the DNA and RNA sequences of the probe are covalently linked.

35. The kit of claim 31, wherein the detectable label on the probe is a fluorescent label.

36. The kit of claim 31, wherein the probe is labeled with a FRET pair.

37. The kit of claim 31, wherein the probe or PCR fragment is linked to a solid support.

38. The kit of claim 31, wherein the kit further comprises an amplification buffer.

39. The kit of claim 31, wherein the amplifying polymerase activity is the activity of a thermostable DNA polymerase.

40. The kit of claim 31, wherein the RNAse H activity is the activity of a thermostable RNAse H.

41. The kit of claim 31, wherein the RNAse H activity is a hot start RNAse H activity.

42. The kit of claim 31, wherein the probe comprises the sequence of SEQ ID NO: 7.

43. A kit for the real-time detection of *Salmonella* in a sample, comprising:
    a) a reverse transcriptase activity for the reverse transcription of a target *Salmonella* invA RNA sequence to produce a target cDNA sequence;
    b) a pair of amplification primers that can anneal to the target cDNA sequence, wherein the pair of amplification primers is the pair of primers of SEQ ID NOs: 1 and 2;
    c) an amplifying activity for the PCR amplification of the target cDNA sequence between the pair of amplification primers to produce a *Salmonella* invA PCR fragment;
    d) a probe comprising a detectable label and DNA and RNA nucleic acid sequences that are substantially complementary to DNA sequences within the PCR fragment; and
    e) an RNAse H activity.

44. The kit of claim 43, further comprising positive, internal, and negative controls.

45. The kit of claim 43, further comprising uracil-N-glycosylase.

46. The kit of claim 43, wherein the DNA and RNA sequences of the probe are covalently linked.

47. The kit of claim 43, wherein the detectable label on the probe is a fluorescent label.

48. The kit of claim 43, wherein the probe is labeled with a FRET pair.

49. The kit of claim 42, wherein the probe or PCR fragment is linked to a solid support.

50. The kit of claim 43, wherein the kit further comprises an amplification buffer.

51. The kit of claim 43, wherein the kit further comprises an amplifying polymerase activity.

52. The kit of claim 43, wherein the RNAse H activity is the activity of a thermostable RNAse H.

53. The kit of claim 43, wherein the RNAse H activity is a hot start RNAse H activity.

54. The kit of claim 43, wherein the probe comprises the sequence of SEQ ID NO: 7.

* * * * *